United States Patent
Dunman et al.

(10) Patent No.: US 10,471,028 B2
(45) Date of Patent: Nov. 12, 2019

(54) SMALL MOLECULE EFFLUX PUMP INHIBITORS

(71) Applicant: UNIVERSITY OF ROCHESTER, Rochester, NY (US)

(72) Inventors: Paul M. Dunman, Pittsford, NY (US); Catlyn E. Blanchard, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 15/317,811

(22) PCT Filed: Jun. 12, 2015

(86) PCT No.: PCT/US2015/035534
§ 371 (c)(1),
(2) Date: Dec. 9, 2016

(87) PCT Pub. No.: WO2015/191988
PCT Pub. Date: Dec. 17, 2015

(65) Prior Publication Data
US 2017/0100414 A1    Apr. 13, 2017

Related U.S. Application Data

(60) Provisional application No. 62/011,613, filed on Jun. 13, 2014.

(51) Int. Cl.
*A61K 31/18* (2006.01)
*A61K 31/00* (2006.01)
(Continued)

(52) U.S. Cl.
CPC .............. *A61K 31/18* (2013.01); *A61K 31/00* (2013.01); *A61K 31/15* (2013.01); *A61K 31/166* (2013.01);
(Continued)

(58) Field of Classification Search
CPC .... A61K 31/65; A61K 31/216; A61K 31/235; A61K 31/34; A61K 31/352
(Continued)

(56) References Cited

U.S. PATENT DOCUMENTS

| 8,785,499 B2 * | 7/2014 | Mackerell, Jr. | ....... C07C 251/86 514/614 |
| 2003/0220338 A1 | 11/2003 | Watkins et al. | |

(Continued)

FOREIGN PATENT DOCUMENTS

| CN | 1188512 | 7/1998 |
| CN | 1976703 | 6/2007 |

(Continued)

OTHER PUBLICATIONS

"Rote Liste 1998. Arzneimittelverzeichnis des Bundesverbandes der Pharmazeutischen Industrie", ECV Editio Cantor Aulendorf/Wurtt, 1998, 2 pages.
(Continued)

*Primary Examiner* — Craig D Ricci
*Assistant Examiner* — Janet L. Coppins
(74) *Attorney, Agent, or Firm* — Kilpatrick Townsend & Stockton LLP

(57) ABSTRACT

Small molecule efflux pump inhibitors are provided, as well as methods for their use in treating infections. Also provided herein are methods of using the small molecule efflux pump inhibitors to restore the antibiotic susceptibility of microbes.

8 Claims, 5 Drawing Sheets

(51) Int. Cl.
| | |
|---|---|
| A61K 31/357 | (2006.01) |
| A61K 31/427 | (2006.01) |
| A61K 31/4422 | (2006.01) |
| A61K 31/63 | (2006.01) |
| A61K 31/635 | (2006.01) |
| A61K 31/15 | (2006.01) |
| A61K 31/166 | (2006.01) |
| A61K 31/216 | (2006.01) |
| A61K 31/235 | (2006.01) |
| A61K 31/352 | (2006.01) |
| A61K 31/402 | (2006.01) |
| A61K 31/4155 | (2006.01) |
| A61K 31/428 | (2006.01) |
| A61K 31/437 | (2006.01) |
| A61K 31/438 | (2006.01) |
| A61K 31/65 | (2006.01) |

(52) U.S. Cl.
CPC .......... *A61K 31/216* (2013.01); *A61K 31/235* (2013.01); *A61K 31/352* (2013.01); *A61K 31/357* (2013.01); *A61K 31/402* (2013.01); *A61K 31/4155* (2013.01); *A61K 31/427* (2013.01); *A61K 31/428* (2013.01); *A61K 31/437* (2013.01); *A61K 31/438* (2013.01); *A61K 31/4422* (2013.01); *A61K 31/63* (2013.01); *A61K 31/635* (2013.01); *A61K 31/65* (2013.01)

(58) Field of Classification Search
USPC ........................................ 514/154
See application file for complete search history.

(56) References Cited

U.S. PATENT DOCUMENTS

| | | | | |
|---|---|---|---|---|
| 2012/0165276 A1* | 6/2012 | Glinka | .................. | C07C 237/22 514/21.9 |
| 2012/0190708 A1 | 7/2012 | Mackerell, Jr. et al. | | |
| 2013/0316943 A1* | 11/2013 | Glinka | .................... | C07F 5/025 514/3.1 |

FOREIGN PATENT DOCUMENTS

| | | |
|---|---|---|
| CN | 101301289 | 11/2008 |
| CN | 103156844 | 6/2013 |
| JP | 11503913 | 4/1999 |
| WO | 9633285 | 10/1996 |
| WO | 2006018544 | 2/2006 |
| WO | 2014022923 | 2/2014 |

OTHER PUBLICATIONS

Blanchard et al., "Identification of Acinetobacter baumannii serum-associated antibiotic efflux pump inhibitors", Antimicrob Agents Chemother., vol. 58, No. 11, Nov. 2014, pp. 6360-6370.
Cai et al., "Development of a liquid chromatography/mass spectrometry-based drug accumulation assay in Pseudomonas aeruginosa", Anal Biochem, vol. 385(2), 2009, pp. 321-325.
Choi et al., "Acinetobacter baumannii invades epithelial cells and outer membrane protein A mediates interactions with epithelial cells", BMC Microbiol, vol. 8, 2008, p. 216.
Chusri et al., "Enhancing antibiotic activity: a strategy to control acinetobacter infections", Journal of Antimicrobial Chemotherapy, vol. 64, No. 6, Dec. 2009, pp. 1203-1211.
Cortez-Cordova et al., "Activity of the efflux pump inhibitor phenylalanine-arginine beta-naphthylamide against the AdeFGH pump of Acinetobacter baumannii", Int J Antimicrob Agents, vol. 37(5), 2011, pp. 420-424.
Coyne et al., "Efflux-mediated antibiotic resistance in *Acinetobacter* spp", Antimicrob Agents Chemother, vol. 55(3), 2011, pp. 947-953.
Coyne et al., "Overexpression of resistance-nodulation-cell division pump AdeFGH confers multidrug resistance in Acinetobacter baumannii", Antimicrob Agents Chemother, vol. 54(10), 2010, pp. 4389-4393.
Damier-Piolle et al., "AdeIJK, a resistance-nodulation-cell division pump effluxing multiple antibiotics in Acinetobacter baumannii", Antimicrob Agents Chemother, vol. 52(2), 2008, pp. 557-562.
Doi et al., "Extensively drug-resistant Acinetobacter baumannii", Emerg Infect Dis, vol. 15(6), 2009, pp. 980-982.
Elkins et al., "Chimeric analysis of AcrA function reveals the importance of its C-terminal domain in its interaction with the AcrB multidrug efflux pump", 2003, pp. 5349-5356.
Fernandez et al., "Adaptive and mutational resistance: role of porins and efflux pumps in drug resistance", Clin Microbiol Ref, vol. 25(4), 2012, pp. 661-681.
Fournier et al., "Comparative genomics of multidrug resistance in Acinetobacter baumannii", PLoS Genet, vol. 2(1), 2006, p. e7.
Garnacho-Montero et al., "Acinetobacter baumannii ventilator-associated pneumonia: epidemiological and clinical findings", Intensive Care Med, vol. 31(5), 2005, pp. 649-655.
Grosso et al., "Emergence of an extreme-drug-resistant (XDR) Acinetobacter baumannii carrying blaOXA-23 in a patient with acute necrohaemorrhagic pancreatitis", J Hosp Infect, vol. 75(1), 2010, pp. 82-83.
Hampton, "Report reveals scope of US antibiotic resistance threat", JAMA, vol. 310(16), 2013, pp. 1661-1663.
Holloway et al., "Genome organization in Pseudomonas", Annu Rev Microbiol, vol. 40, 1986, pp. 79-105.
Hood et al., "Acinetobacter baumannii increases tolerance to antibiotics in response to monovalent cations", Antimicrob Agents Chemother, vol. 54(3), 2010, pp. 1029-1041.
Hornsey et al., "AdeABC-mediated efflux and tigecycline MICs for epidemic clones of Acinetobacter baumannii", J. Antimicrob Chemother, vol. 65(8), 2010, pp. 1589-1593.
Howard et al., "Acinetobacter baumannii: an emerging opportunistic pathogen", Virulence, vol. 3(3), 2012, pp. 243-250.
Hujer et al., "Analysis of antibiotic resistance genes in multidrug-resistant *Acinetobacter* sp. isolates from military and civilian patients treated at the Walter Reed Army Medical Center", Antimicrob Agents Chemother, vol. 50(12), 2006, pp. 4114-4123.
Jacobs et al., "Characterization of the Acinetobacter baumannii growth phase-dependent and serum responsive transcriptomes", FEMS Immunol Med Microbiol, vol. 64(3), 2012, pp. 403-412.
Jacobs et al., "Inactivation of phospholipase D diminishes Acinetobacter baumannii pathogenesis", pathogenesis. Infect Immun, vol. 78(5), 2010, pp. 1952-1962.
Kim et al., "Serum resistance of Acinetobacter baumannii through the binding of factor H to outer membrane proteins", FEMS Microbiol Lett, vol. 301(2), 2009, pp. 224-231.
Koh et al., "Programmed cell death: its possible contribution to neurotoxicity mediated by calcium channel antagonists", Brain Res, vol. 587(2), 1992, pp. 233-240.
Lomovskaya et al., "Identification and characterization of inhibitors of multidrug resistance efflux pumps in Pseudomonas aeruginosa: novel agents for combination therapy", Antimicrob Agents Chemother, vol. 45(1), 2001, pp. 105-106.
Magnet et al., "Resistance-nodulation-cell division-type efflux pump involved in aminoglycoside resistance in Acinetobacter baumannii strain BM4454", Antimicrob Agents Chemother, vol. 45(12), 2001, pp. 3375-3380.
Marchand et al., "Expression of the RND-type efflux pump AdeABC in Acinetobacter baumannii is regulated by the AdeRS two-component system", Antimicrob Agents Chemother, vol. 48(9), 2004, pp. 3298-3304.
PCT/US2015/035534, "International Preliminary Report on Patentability", dated Dec. 22, 2016, 17 pages.
PCT/US2015/035534, "International Search Report and Written Opinion", dated Nov. 18, 2015, 26 pages.
PCT/US2015/035534, "Invitation to Pay Add'l Fees and Partial Search Report", Sep. 4, 2015, 10 pages.

(56) References Cited

OTHER PUBLICATIONS

Peleg et al., "Acinetobacter baumannii: emergence of a successful pathogen", Clin Microbiol Rev, vol. 21(3), 2008, pp. 538-582.

Peleg et al., "Tigecycline Efflux as a Mechanism for Nonsusceptibility in Acinetobacter baumannii," Antimicrob Agents Chemother, vol. 51(6), 2007, pp. 2065-2069.

Rajamohan et al., "Molecular and functional characterization of a novel efflux pump, AmvA, mediating antimicrobial and disinfectant resistance in Acinetobacter baumannii", J Antimicrob Chemother, vol. 65(9), 2010, pp. 1919-1925.

Rice et al., "Federal funding for the study of antimicrobial resistance in nosocomial pathogens: no ESKAPE", J Infect Dis, vol. 197(8), 2008, pp. 1079-1081.

Roca et al., "CraA, a major facilitator superfamily efflux pump associated with chloramphenicol resistance in Acinetobacter baumannii", Antimicrob Agents Chemother, vol. 53(9), 2009, pp. 4013-4014.

Roca et al., "The Acinetobacter baumannii Oxymoron: Commensal Hospital Dweller Turned Pan-Drug-Resistant Menace", Front Microbiol, vol. 3 Article 148, 2012, pp. 1-30.

Rumbo et al., "Contribution of efflux pumps, porins, and beta-lactamases to multidrug resistance in clinical isolates of Acinetobacter baumannii", Antimicrob Agents Chemother, vol. 57(11), 2013, pp. 5247-5257.

Russo et al., "Penicillin-binding protein 7/8 contributes to the survival of Acinetobacter baumannii in vitro and in vivo", J Infect Dis, vol. 199(4), 2009, pp. 513-521.

Russo et al., "The K1 capsular polysaccharide of Acinetobacter baumannii strain 307-0294 is a major virulence factor", Infect Immun, vol. 78(9), 2010, pp. 3993-4000.

Shi et al., "Synthesis and antimicrobial activities of schiff bases derived from 5-chloro-salicylaldehyde", European Journal of Medicinal Chemistry, vol. 42, No. 4, Apr. 2007, pp. 558-564.

Simmonds et al., "Outbreak of Acinetobacter infection in extremely low birth weight neonates", Pediatr Infect Dis J, vol. 28(3), 2009, pp. 210-214.

Srinivasan et al., "Role of AbeS, a novel efflux pump of the SMR family of transporters, in resistance to antimicrobial agents in Acinetobacter baumannii", Antimicrob Agents Chemother, vol. 53(12), 2009, pp. 5312-5316.

Su et al., "AbeM, an H+-coupled Acinetobacter baumannii multidrug efflux pump belonging to the MATE family of transporters", Antimicrob Agents Chemother, vol. 49(10), 2005, pp. 4362-4364.

Sunenshine et al., "Multidrug-resistant Acinetobacter infection mortality rate and length of hospitalization", Emerg Infect Dis, vol. 13(1), 2007, pp. 97-103.

Tan et al., "Comparative genomic analysis of rapid evolution of an extreme-drug-resistant Acinetobacter baumannii clone", Genome Biol Evol, vol. 5(5), 2013, pp. 807-818.

Wang et al., "Community-acquired Acinetobacter baumannii bacteremia in adult patients in Taiwan", J. Clin. Microbiol, vol. 40(4), 2002, pp. 1526-1529.

Watkins et al., "The relationship between physicochemical properties, in vitro activity and pharmacokinetic profiles of analogues of diamine-containing efflux pump inhibitors", Bioorg Med Chem Lett, vol. 13(23), 2003, pp. 4241-4244.

Wieczorek et al., "Multidrug resistant Acinetobacter baumannii—the role of AdeABC (RND family) efflux pump in resistance to antibiotics", Folia Histochem Cytobiol, vol. 46(3), 2008, pp. 257-267.

Wisplinghoff et al., "Nosocomial bloodstream infections in US hospitals: analysis of 24,179 cases from a prospective nationwide surveillance study", Clin Infect Dis, vol. 39(3), 2004, pp. 309-317.

Yang et al., "Assessment of the effect of efflux pump inhibitors on in vitro antimicrobial susceptibility of multidrug-resistant acinetobacter baumannii", International Journal of Antimicrobial Agents, vol. 42, No. 3, Sep. 2013, pp. 283-284.

Zgurskaya et al., "AcrA is a highly asymmetric protein capable of spanning the periplasm", J. Mol. Biol., vol. 285(1), 1999, pp. 409-420.

Washington JA. Principles of Diagnosis. In: Baron S, editor. Medical Microbiology. 4th edition. Galveston (TX): University of Texas Medical Branch at Galveston; 1996. Chapter 10. Available from: https://www.ncbi.nlm.nih.gov/books/NBK8014/.

CN201580030544.5, "Office Action," dated Sep. 25, 2018, 12 total pages (6 pages in Chinese language and 6 pages of English language translation).

Rote Liste 1998, Arzneimittelverzeichnisdes Bundesverbandes der Pharmazeutischen Industrie, 1998, formulation 68011.

EP15735770.8, "Office Action", dated Mar. 18, 2019, 7 pages.

JP2016-572622, "Office Action", dated Mar. 6, 2019, 7 pages.

Kalle et al., "Inhibition of Bacterial Multidrug Resistance by Celecoxib, a Cyclooxygenase-2 Inhibitor", Antimicrobial Agent and Chemotherapy, vol. 55, No. 1, 2011, pp. 439-442.

\* cited by examiner

SMALL MOLECULE EFFLUX PUMP INHIBITORS

CROSS REFERENCE TO PRIORITY APPLICATION

This application claims priority to U.S. Provisional Application No. 62/011,613, filed Jun. 13, 2014, which is incorporated herein by reference in its entirety.

BACKGROUND

*Acinetobacter baumannii* has emerged as a major nosocomial pathogen that can cause ventilator associated pneumonia (VAP) and bacteremia, with associated mortality rates as high as 60% among susceptible patient populations. The high rates of *A. baumannii* associated morbidity and mortality have been largely attributed to the emergence of antibiotic resistance that has compromised the effectiveness of currently available antibiotics. The Centers for Disease Control and Prevention recently reported that 63% of all *A. baumannii* U.S. infections are caused by multi-drug resistant strains that are resistant to three or more classes of antibiotics and strains that are resistant to all current classes of antibiotics have recently been identified in the U.S. and elsewhere.

*A. baumannii* antibiotic resistance is mediated by an expansive repertoire of enzymatic determinants, such as β-lactamases, and efflux pumps that extrude toxic agents, including antibiotics, from the cell. With regard to the latter, the organism has been shown to harbor representatives of each of the five bacterial drug efflux pump families. For instance, CraA and AmvA are major facilitator superfamily (MFS) pumps that are proposed to efflux chloramphenicol and erythromycin, respectively; AbeM is a multidrug and toxic compound extrusion (MATE) family protein that effluxes aminoglycosides, quinolones, and chloramphenicol; AbeS is a small multidrug resistance (SMR) family pump that confers resistance to erythromycin and novobiocin as well as low level tolerance to aminoglycosides, quinolones, tetracycline and trimethoprim; AdeABC, AdeFGH, and AdeIJK are resistance nodulation division (RND) family pumps that have been associated with resistance to aminoglycosides, β-lactams, fluoroquinolones, tetracyclines, tigecycline, macrolides, chloramphenicol, and trimethoprim. Furthermore, *A. baumannii* is also known to harbor several ABC family transporters and horizontally acquired Tet efflux pumps belonging to the MFS that confer tetracycline resistance.

In addition to the aforementioned well-characterized efflux pumps, *A. baumannii* is reported to harbor an array of additional putative efflux pumps that may confer antibiotic resistance. For instance, the common laboratory strains, AYE and ATCC17978 contain 46 and 73 genes, respectively, that are annotated as putative drug efflux pumps. It remains to be seen if these factors do indeed modulate antibiotic tolerance or what endogenous- or exogenous-cues modulate their activity. Nonetheless, recent studies suggest that they are likely to have clinical significance. It has been found that 18 previously-uncharacterized putative drug efflux associated factors were significantly upregulated and conferred resistance to levofloxacin and amikacin during *A. baumannii* growth in physiologically relevant salt conditions. Likewise, *A. baumannii* grown in human serum was found to induce expression of approximately 22 drug efflux-associated genes and corresponded to efflux mediated tolerance to minocycline at levels that are clinically relevant. Such regulated changes efflux pump expression and, consequently, activity in response to host-associated environmental cues is thought to temporarily increase a bacterium's ability to survive antibiotic challenge and is hypothesized to allow otherwise clinically defined antibiotic susceptible strains to resist antibiotic insult; this phenomenon has recently been termed adaptive efflux-mediated resistance.

SUMMARY

Described herein are small molecule efflux pump inhibitors. Also described herein are methods of using the small molecule efflux pump inhibitors to restore the antimicrobial susceptibility of microbes.

A pharmaceutical composition described herein includes an efflux pump inhibitor of the following formula:

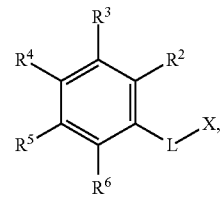

or a pharmaceutically acceptable salt or prodrug thereof, wherein L is a direct bond or a substituted or unsubstituted linking unit; $R^2$, $R^3$, $R^4$, $R^5$, and $R^6$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl; and X is selected from the group consisting of substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted sulfonyl, or substituted or unsubstituted carboxyl; and an antimicrobial agent.

Optionally, the efflux pump inhibitor is

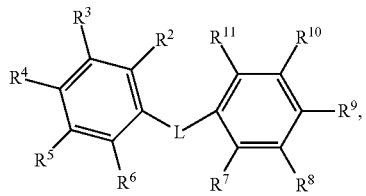

wherein $R^7$, $R^8$, $R^9$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl.

Optionally, the efflux pump inhibitor is

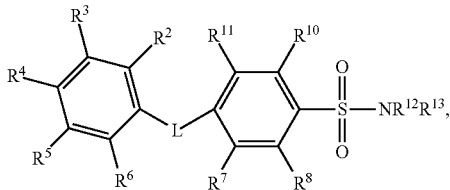

wherein $R^7$, $R^8$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl; and $R^{12}$ and $R^{13}$ are each independently selected from the group consisting of hydrogen, substituted or unsubstituted amidine, substituted or unsubstituted alkyl, substituted or unsubstituted aryl, and substituted or unsubstituted heteroaryl.

Optionally, the efflux pump inhibitor is

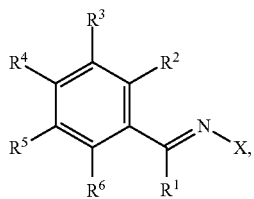

wherein $R^1$ is selected from the group consisting of hydrogen and substituted or unsubstituted alkyl.

Optionally, the efflux pump inhibitor is

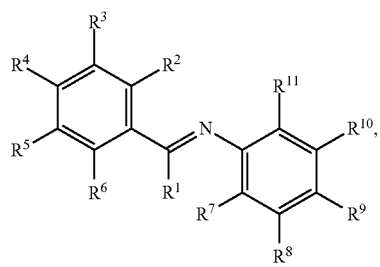

wherein
$R^1$ is selected from the group consisting of hydrogen and substituted or unsubstituted alkyl; and $R^7$, $R^8$, $R^9$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl.

Optionally, the efflux pump inhibitor is

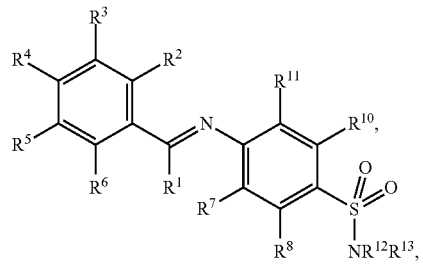

wherein $R^1$ is selected from the group consisting of hydrogen and substituted or unsubstituted alkyl; $R^7$, $R^8$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl; and $R^{12}$ and $R^{13}$ are each independently selected from the group consisting of hydrogen, substituted or unsubstituted amidine, substituted or unsubstituted alkyl, substituted or unsubstituted aryl, and substituted or unsubstituted heteroaryl.

Optionally, the efflux pump inhibitor is

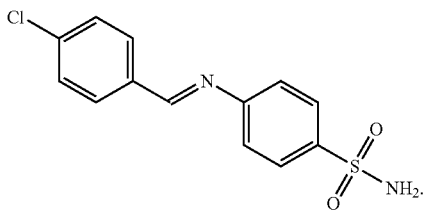 [SMILES: NS(=O)(=O)c1ccc(/N=C/c2ccc(Cl)cc2)cc1]

A pharmaceutical composition described herein includes an efflux pump inhibitor of the following formula:

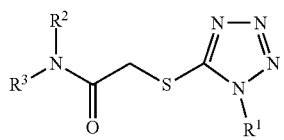

or a pharmaceutically acceptable salt or prodrug thereof, wherein $R^1$, $R^2$, and $R^3$ are each independently selected from hydrogen, substituted alkyl, substituted alkenyl, substituted alkynyl, substituted or unsubstituted aryl, or substituted or unsubstituted heteroaryl; and an antimicrobial agent. Optionally, the efflux pump inhibitor is
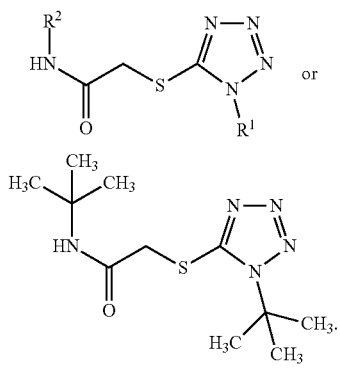
or
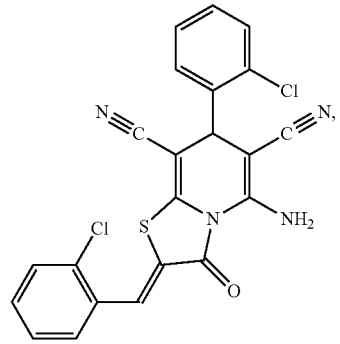
Optionally, the efflux pump inhibitor is selected from the group consisting of:
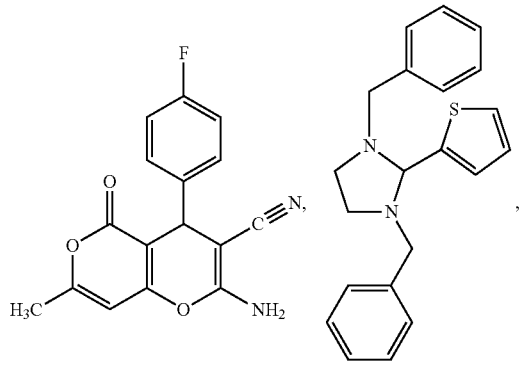
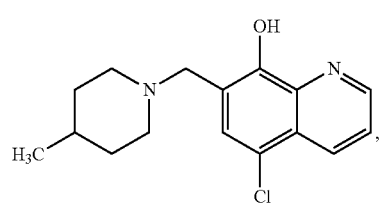
-continued
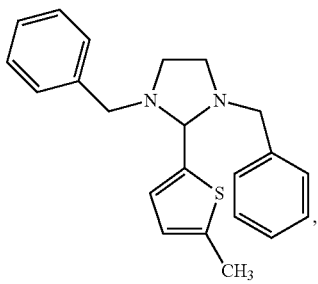
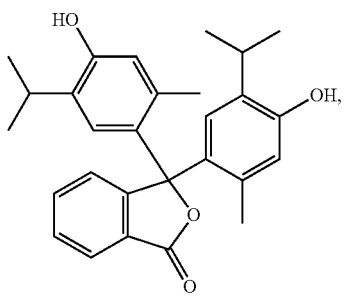
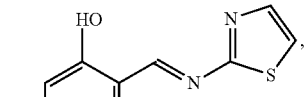
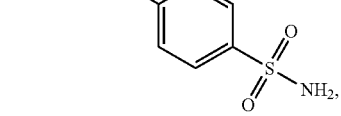
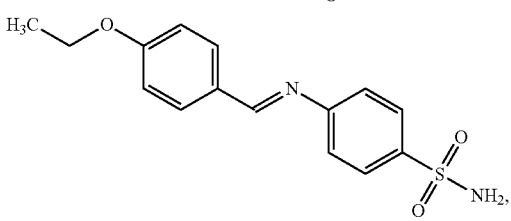
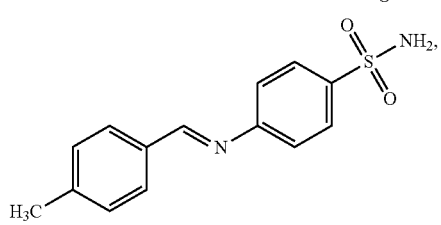
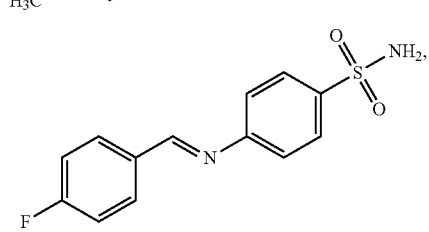

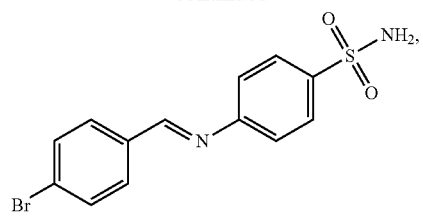
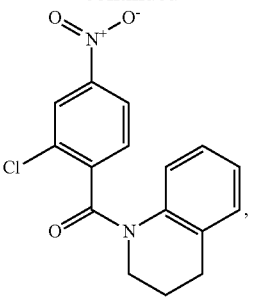
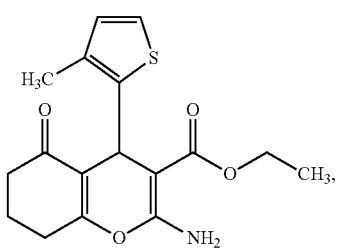
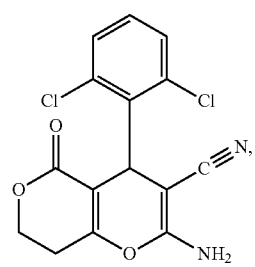
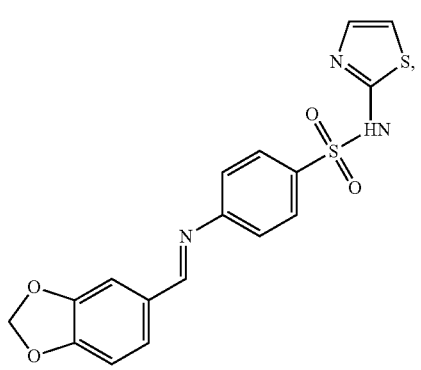
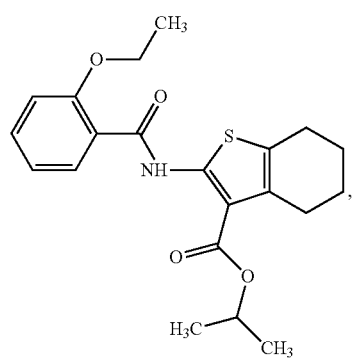
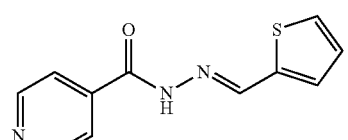
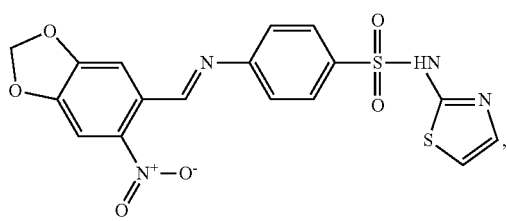
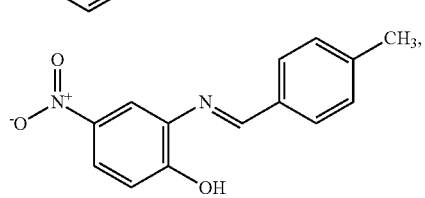
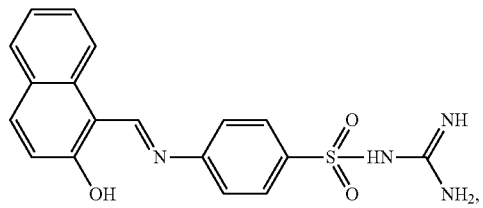
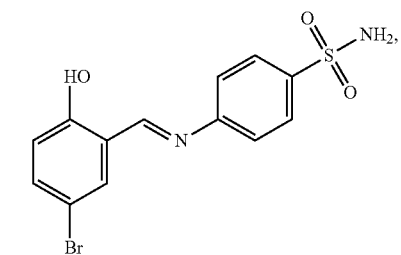
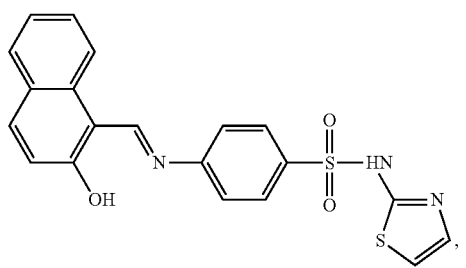

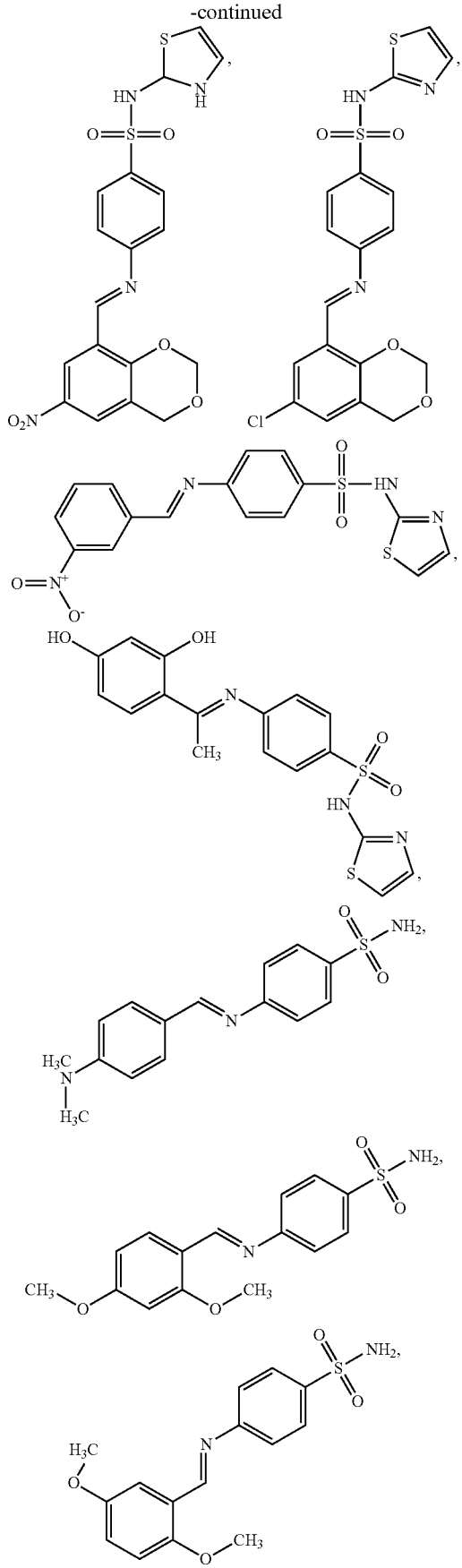
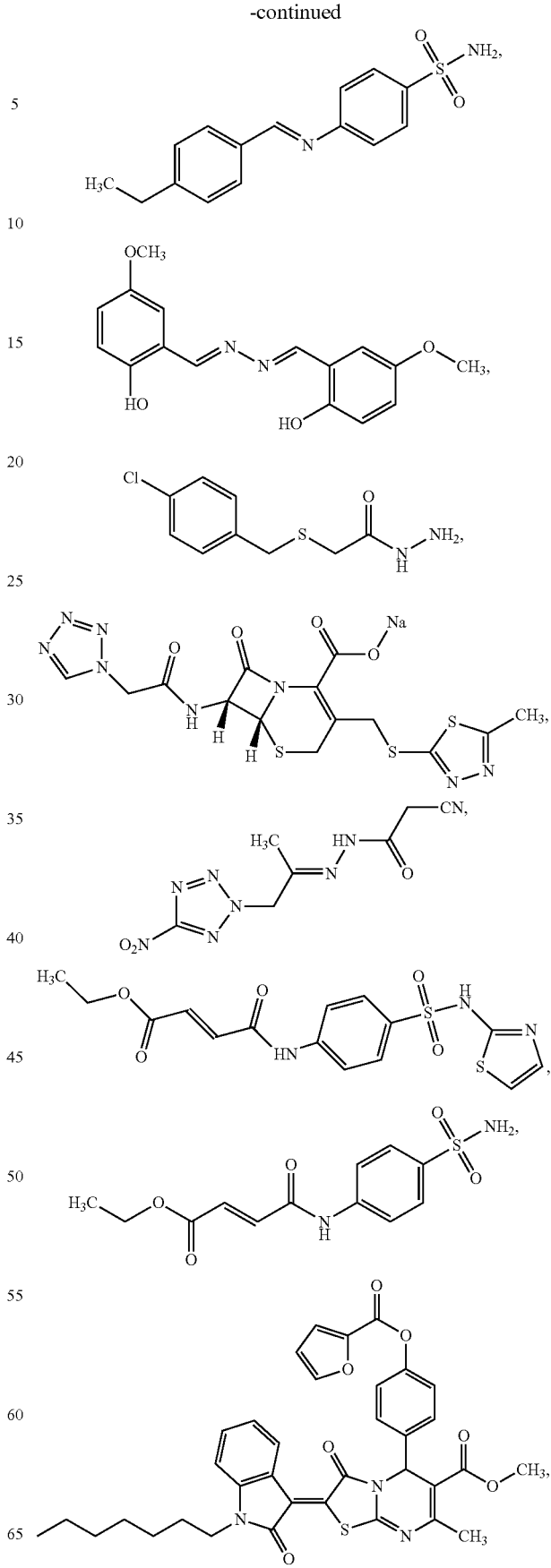

-continued
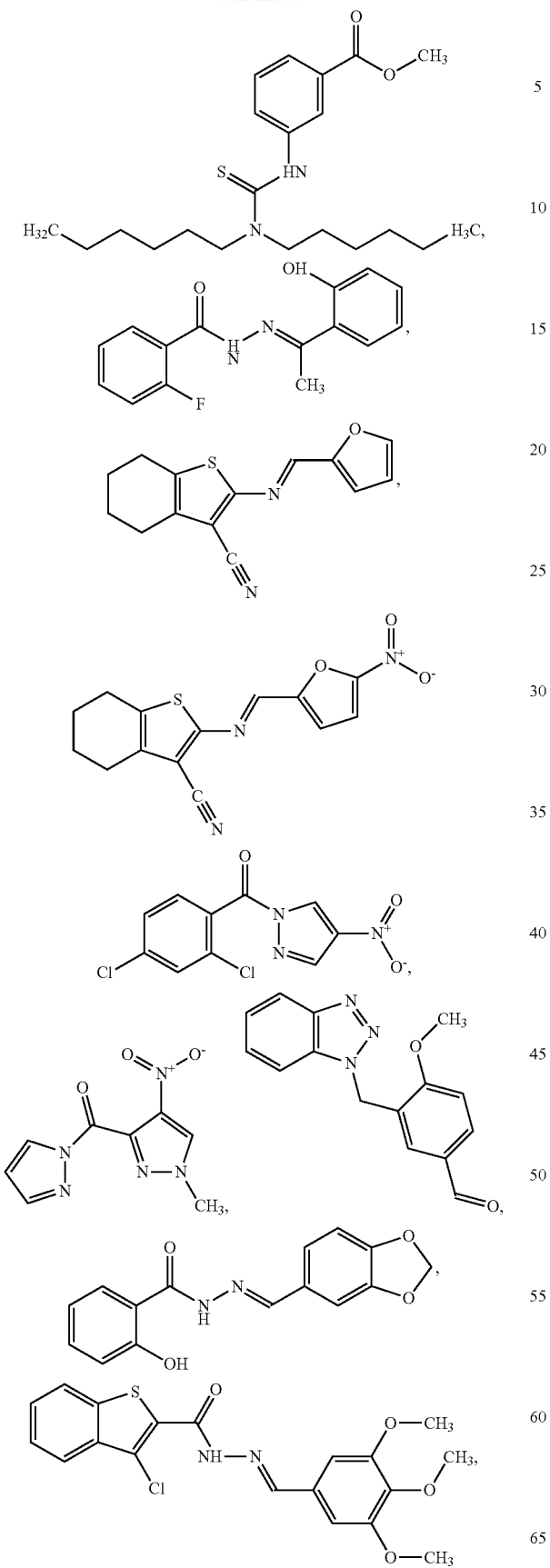
-continued
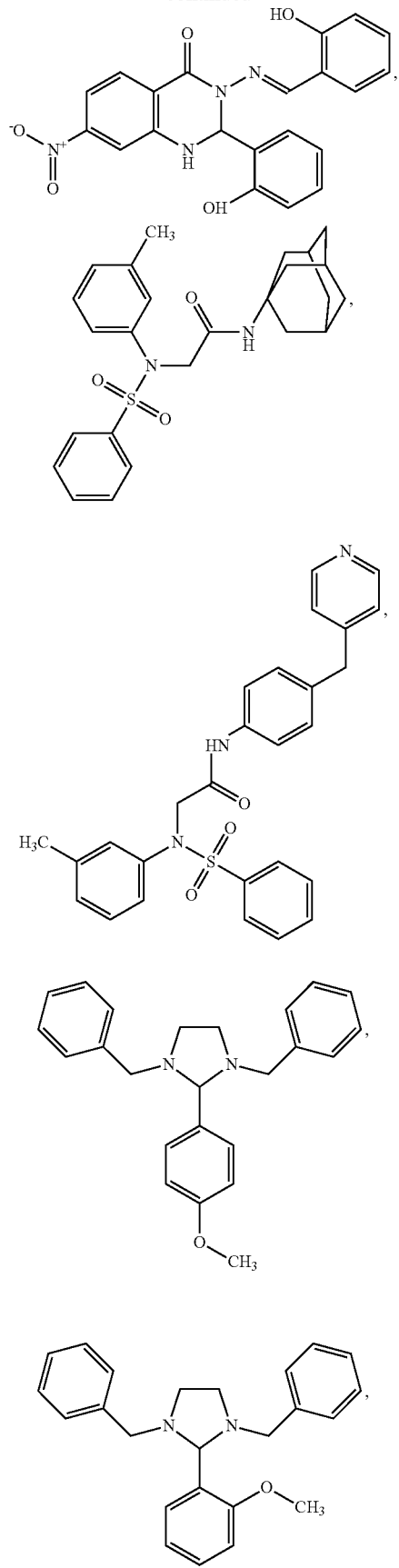

13
-continued
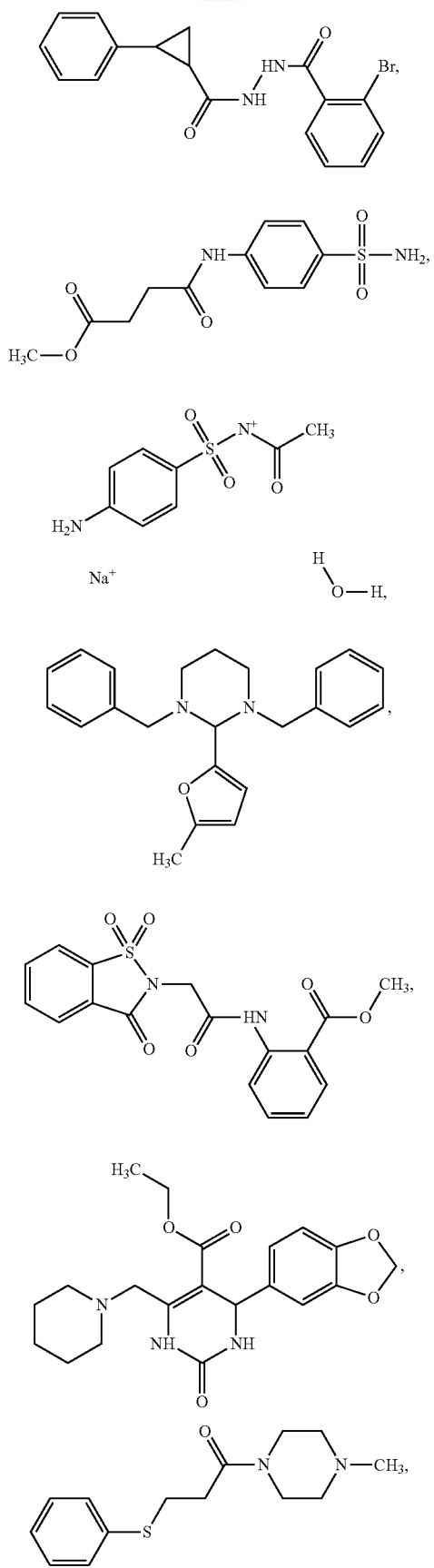
14
-continued
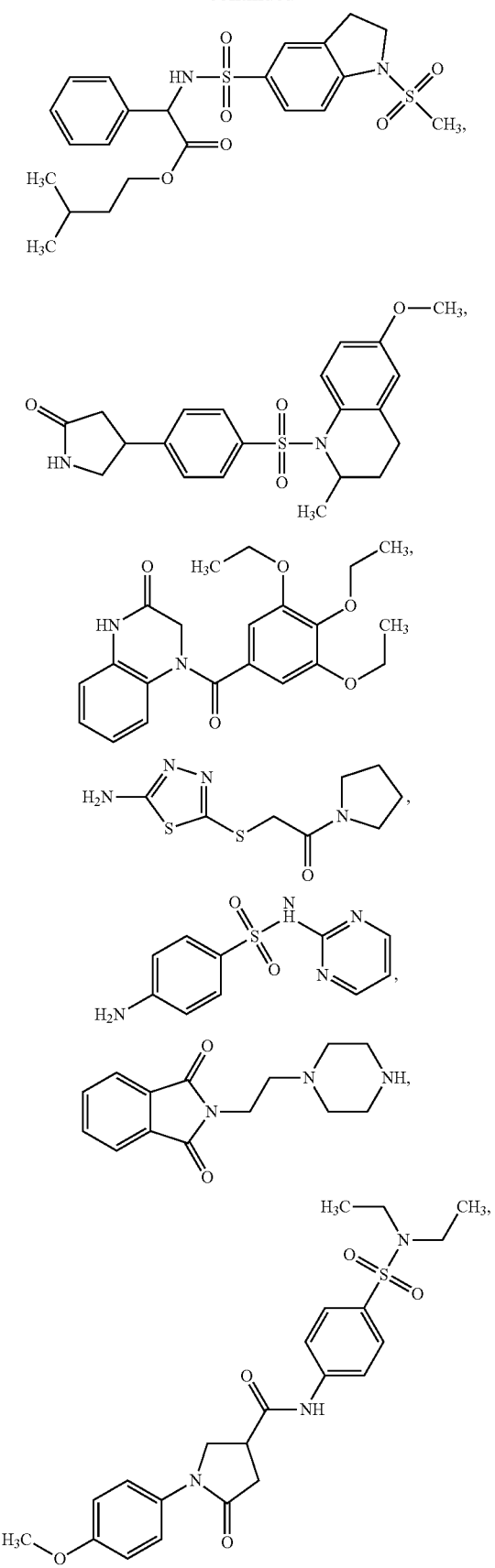

-continued

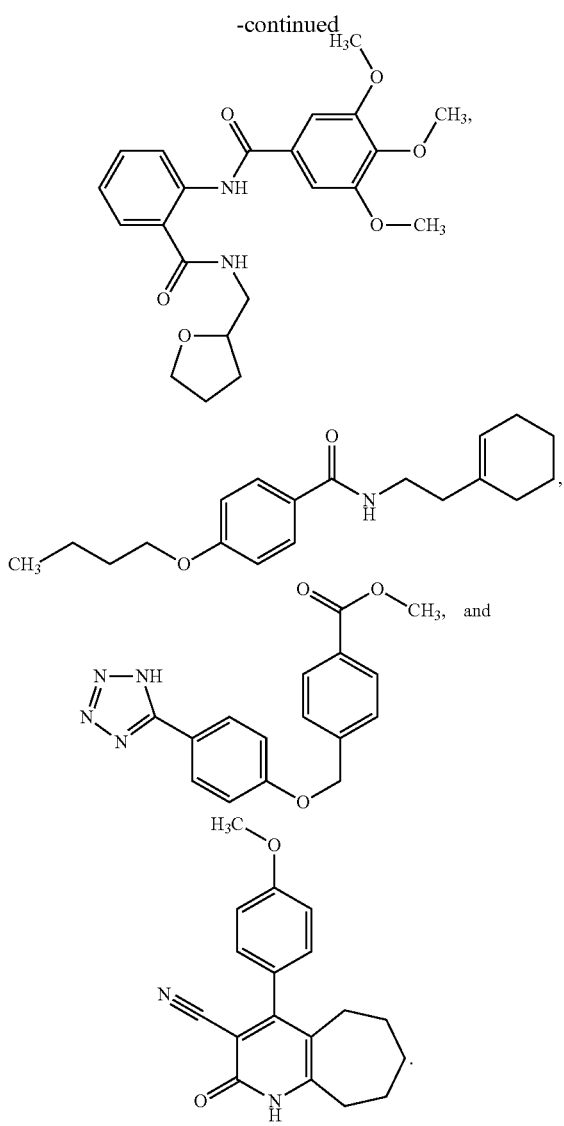

Optionally, the antimicrobial agent is selected from the group consisting of minocycline, ciprofloxacin, levofloxacin, nalidixic acid, amikacin, gentamycin, kanamycin, meropenem, ceftriaxone, erythromycin, colistin polymxin B, sulfamethoxazole, tigecycline, tobramycin, and trimethoprim. Optionally, the composition further includes a pharmaceutically acceptable carrier.

Also described herein are methods for treating a microbial infection in a subject. A method for treating a microbial infection in a subject includes administering to the subject an effective amount of an efflux pump inhibitor as described herein and an antimicrobial agent. Optionally, the antimicrobial agent is selected from the group consisting of minocycline, ciprofloxacin, levofloxacin, nalidixic acid, amikacin, gentamycin, kanamycin, meropenem, ceftriaxone, erythromycin, colistin polymxin B, sulfamethoxazole, tigecycline, tobramycin, and trimethoprim.

Optionally, the methods can further include selecting a subject infected with a microbe that is resistant to the antimicrobial agent. Optionally, the methods can further include selecting a subject infected with a microbe that is capable of developing resistance to the antimicrobial agent. The resistance can be mediated by an efflux pump. The efflux pump inhibitor and the antimicrobial agent can be administered sequentially (in either order) or simultaneously.

Optionally, the microbial infection is a bacterial infection. The bacterial infection can optionally be a gram-negative bacterial infection, such as an *Acinetobacter* bacterial infection (e.g., an *Acinetobacter baumannii* infection) or a *Pseudomonas* bacterial infection (e.g., a *Pseudomonas aeruginosa* infection). The bacterial infection can optionally be a gram-positive bacterial infection.

Further described herein are methods for inhibiting an efflux pump in a cell. A method for inhibiting an efflux pump in a cell includes contacting the cell with an effective amount of an efflux pump inhibitor as described herein. Optionally, the cell is a microbial cell (e.g., a bacterial cell). Optionally, the bacterial cell is a gram-negative bacterial cell. Optionally, the gram-negative bacterial cell is an *Acinetobacter* bacterial cell (e.g., an *Acinetobacter baumannii* bacterial cell) or a *Pseudomonas* bacterial cell (e.g., a *Pseudomonas aeruginosa* bacterial cell). Optionally, the bacterial cell is a gram-positive bacterial cell.

The details of one or more embodiments are set forth in the drawings and the description below. Other features, objects, and advantages will be apparent from the description and drawings, and from the claims.

DESCRIPTION OF DRAWINGS

FIG. 3, Panel B is a graph of *Pseudomonas aeruginosa* strain PA01 growth, supplemented with increasing concentrations of ciprofloxacin, in LB broth and human serum. Efflux was inhibited with the known efflux pump inhibitor reserpine (grey triangles), ABEPI1 (grey X), and ABEPI2 (black circles). The asterisks indicate statistically significant differences between LB growth and serum growth as determined by Student's t-test (*$P<0.05$, **$P<0.01$). FIG. 3. Panel C contains the structures of ABEPI1 and ABEPI2.

Figure 1:
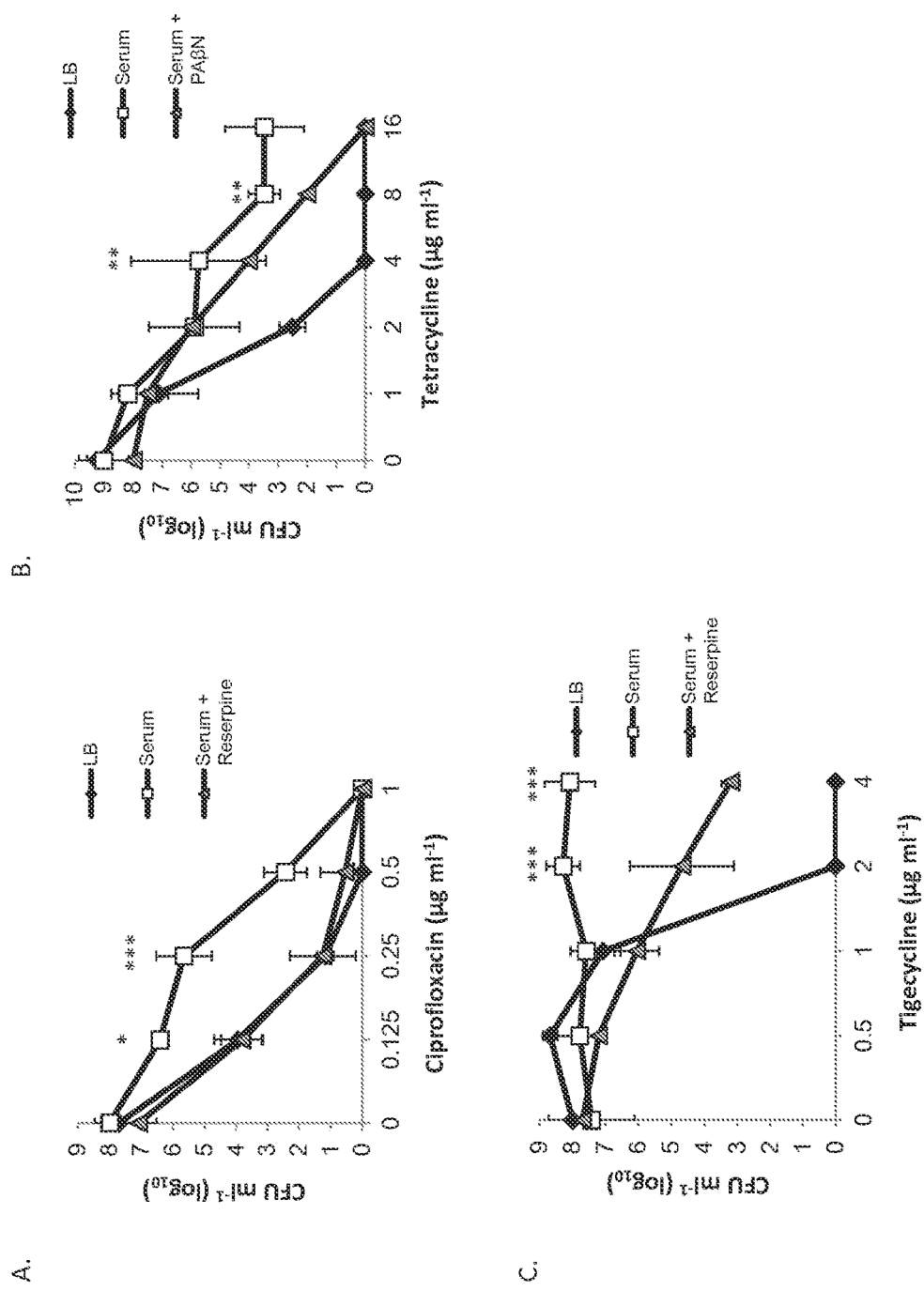
FIG. 1 contains graphs comparing the growth of *Acinetobacter baumannii* strain 98-37-09 in Luria-Bertani (LB) broth, in human serum, and in serum with efflux pump inhibitor reserpine supplemented with increasing concentrations of ciprofloxacin (Panel A), tetracycline (Panel B), or tigecycline (Panel C). The asterisks indicate statistically significant differences between LB growth and serum growth as determined by Student's t-test (*$P<0.05$, $P<0.01$, *$P<0.001$).

Cells were treated with carbachol alone (Panel A), verapamil (Panel B), ABEPI1 (Panel C), or ABEPI2 (Panel D) after 15 seconds of fluorescent monitoring (black arrows). After 60 seconds, all wells were stimulated with carbachol (grey arrows).

DETAILED DESCRIPTION

Described herein are small molecule efflux pump inhibitors. Optionally, the efflux pump inhibitors are microbial efflux pump inhibitors (e.g., antibiotic efflux pump inhibitors).

Optionally, the efflux pump inhibitors are mammalian efflux pump inhibitors. Also described herein are methods of using the small molecule efflux pump inhibitors to restore the antibiotic susceptibility of microbes, such as Gram-negative bacterial pathogens (e.g., *Acinetobacter baumannii* and *Pseudomonas aeruginosa*). The compounds described herein lack the problems commonly associated with other classes of efflux pump inhibitors, namely, significant mammalian cytotoxicity and calcium channel inhibition. These compounds can be used as adjunctive therapy to potentiate the activity of current and future antibiotics for the therapeutic intervention of bacterial infections (e.g., Gram-negative bacterial infections and Gram-positive bacterial infections).

I. Compounds

A class of efflux pump inhibitors useful in the methods described herein comprises compounds represented by Formula I:

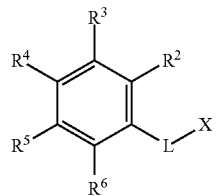

or a pharmaceutically acceptable salt or prodrug thereof.

In Formula I, L is a direct bond or a substituted or unsubstituted linking unit. As used herein, the term direct bond indicates a covalent bond between the carbon on the six-member ring structure to which L is shown to be attached and X or an atom of X. When L is a substituted or unsubstituted linking unit, it is a linking unit having 1 to 4 carbon atoms and up to 2 heteroatoms (e.g., oxygen, nitrogen, or sulfur). Examples of L as a substituted or unsubstituted linking unit include substituted or unsubstituted alkyl groups (e.g., methyl; ethyl; propyl; butyl; —C(O)—; —CH$_2$(O)—; or —C(O)CH$_2$—), substituted or unsubstituted alkenyl groups (e.g., =CH—; =CHCH$_2$—; =CHCH$_2$CH$_2$—; or =CHCH$_2$CH$_2$CH$_2$—), substituted or unsubstituted alkynyl groups, substituted or unsubstituted heteroalkyl groups with up to 2 heteroatoms (e.g., —NH—; —CH$_2$NH—; —NHCH$_2$—; —NHC(O)—; —C(O)NH—; —CH$_2$NHC(O)—; —CH$_2$C(O)NH—; —NHC(O)CH$_2$—; or —C(O)NHCH$_2$—), substituted or unsubstituted heteroalkenyl groups with up to 2 heteroatoms (e.g., =N— or —N=), and substituted or unsubstituted heteroalkynyl groups with up to 2 heteroatoms.

Optionally, L can be substituted by a $R^1$ group. In Formula I, $R^1$ is selected from the group consisting of hydrogen and substituted or unsubstituted alkyl. Optionally, $R^1$ is hydrogen or methyl.

Additionally in Formula I, $R^2$, $R^3$, $R^4$, $R^5$, and $R^6$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl. Optionally, one or more of $R^2$, $R^3$, $R^4$, $R^5$, and $R^6$ is hydrogen, a halogen (e.g., bromo, chloro, or fluoro), hydroxyl, methoxy, ethoxy, methyl, ethyl, nitro, amino, or dimethylamino.

Also, in Formula I, X is selected from the group consisting of substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted sulfonyl, or substituted or unsubstituted carboxyl. Optionally, X is substituted or unsubstituted aryl or substituted or unsubstituted heteroaryl. For example, X can optionally be a five-membered ring, a six-membered ring, or a seven-membered ring. Optionally, X is substituted or unsubstituted phenyl. Optionally, X is substituted or unsubstituted thiazole. Optionally, X includes a substituted or unsubstituted sulfonyl. For example, X can include a sulfonamide group.

Optionally, in Formula I, adjacent R groups combine to form a substituted or unsubstituted cycloalkyl, substituted or unsubstituted heterocycloalkyl, substituted or unsubstituted aryl, and/or substituted or unsubstituted heteroaryl. For example, in Formula I, $R^2$ and $R^3$, $R^3$ and $R^4$, $R^4$ and $R^5$, or $R^5$ and $R^6$ can combine to form a substituted or unsubstituted cycloalkyl, substituted or unsubstituted heterocycloalkyl, substituted or unsubstituted aryl, and/or substituted or unsubstituted heteroaryl.

In some examples of Formula I, X is substituted or unsubstituted aryl. Optionally, X is a substituted or unsubstituted phenyl to provide Structure I-A:

Structure I-A

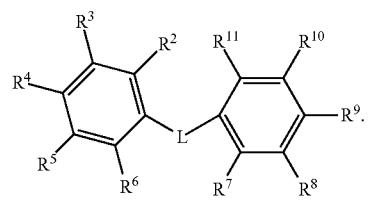

In Structure I-A. $R^1$, $R^2$, $R^3$, $R^4$, $R^5$, and $R^6$ are as defined in Formula I. Also in Structure I-A, $R^7$, $R^8$, $R^9$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl. Optionally, $R^9$ is selected from hydrogen, sulfonamide, or methyl.

Optionally, in Structure I-A, adjacent R groups combine to form a substituted or unsubstituted cycloalkyl, substituted or unsubstituted heterocycloalkyl, substituted or unsubstituted aryl, and/or substituted or unsubstituted heteroaryl. For example, in Structure I-A, $R^2$ and $R^3$, $R^3$ and $R^4$, $R^4$ and $R^5$, $R^5$ and $R^6$, $R^7$ and $R^8$, $R^8$ and $R^9$, $R^9$ and $R^{10}$, and/or $R^{10}$ and $R^{11}$ can combine to form a substituted or unsubstituted cycloalkyl, substituted or unsubstituted heterocycloalkyl, substituted or unsubstituted aryl, or substituted or unsubstituted heteroaryl.

In Structure I-A, $R^9$ can be a substituted or unsubstituted sulfonamide according to Structure I-B:

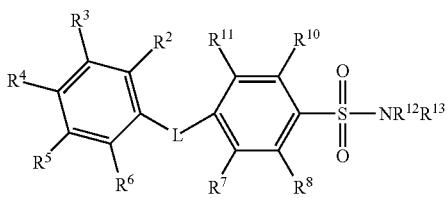

Structure I-B

In Structure I-B, $R^1$, $R^2$, $R^3$, $R^4$, $R^5$, $R^6$, $R^7$, $R^8$, $R^{10}$, and $R^{11}$ are as defined in Formula I. Also in Structure I-B, $R^{12}$ and $R^{13}$ are each independently selected from the group consisting of hydrogen, substituted or unsubstituted amidine, substituted or unsubstituted alkyl, substituted or unsubstituted aryl, and substituted or unsubstituted heteroaryl.

In some examples of Formula I, X is a substituted or unsubstituted heteroaryl. Optionally, X is a substituted or unsubstituted thiazole according to Structure I-C:

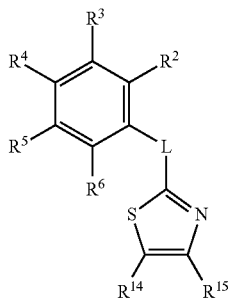

Structure I-C

In Structure I-C, $R^1$, $R^2$, $R^3$, $R^4$, $R^5$, and $R^6$ are defined as in Formula I. Also, in Structure I-C, $R^{14}$ and $R^{15}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl. Optionally, $R^{14}$ and $R^{15}$ are hydrogen.

In some examples of Formula I, L is a substituted or unsubstituted heteroalkenyl group containing a nitrogen atom. Optionally, L is —C($R^1$)=N- to provide Structure I-D:

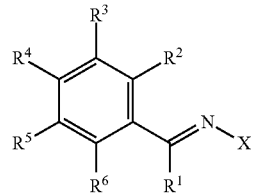

Structure I-D

In Structure I-D, $R^1$, $R^2$, $R^3$, $R^4$, $R^5$, $R^6$, and X are as defined in Formula I.

In some examples of Structure I-D, X is substituted or unsubstituted aryl. Optionally, X is a substituted or unsubstituted phenyl to provide Structure I-E:

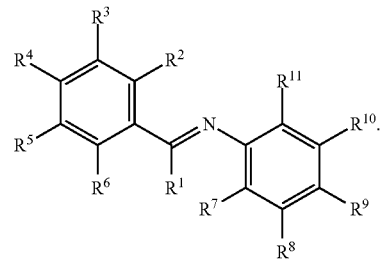

Structure I-E

In Structure I-E, $R^1$, $R^2$, $R^3$, $R^4$, $R^5$, and $R^6$ are as defined in Formula I. Also in Structure I-E, $R^7$, $R^8$, $R^9$, $R^{10}$, and $R^{11}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl. Optionally, $R^9$ is selected from hydrogen, sulfonamide, or methyl.

Optionally, in Structure I-E, adjacent R groups combine to form a substituted or unsubstituted cycloalkyl, substituted or unsubstituted heterocycloalkyl, substituted or unsubstituted aryl, and/or substituted or unsubstituted heteroaryl. For example, in Structure I-E, $R^2$ and $R^3$, $R^3$ and $R^4$, $R^4$ and $R^5$, $R^5$ and $R^6$, $R^7$ and $R^8$, $R^8$ and $R^9$, $R^9$ and $R^{10}$, and/or $R^{10}$ and $R^{11}$ can combine to form a substituted or unsubstituted cycloalkyl, substituted or unsubstituted heterocycloalkyl, substituted or unsubstituted aryl, or substituted or unsubstituted heteroaryl.

In Structure I-E, $R^9$ can be a substituted or unsubstituted sulfonamide according to Structure I-F:

Structure I-F

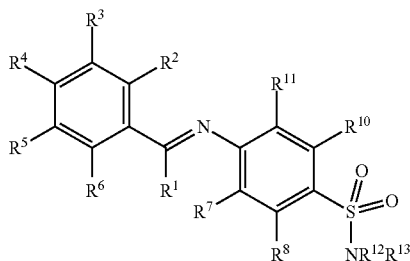

In Structure I-F, $R^1$, $R^2$, $R^3$, $R^4$, $R^5$, $R^6$, $R^7$, $R^8$, $R^{10}$, and $R^{11}$ are as defined in Formula I. Also in Structure I-F, $R^{12}$ and $R^{13}$ are each independently selected from the group consisting of hydrogen, substituted or unsubstituted amidine, substituted or unsubstituted alkyl, substituted or unsubstituted aryl, and substituted or unsubstituted heteroaryl.

In some examples of Structure I-D, X is a substituted or unsubstituted heteroaryl. Optionally, X is a substituted or unsubstituted thiazole according to Structure I-G:

Structure I-G

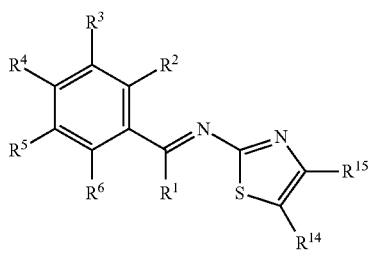

In Structure I-G, $R^1$, $R^2$, $R^3$, $R^4$, $R^5$, and $R^6$ are defined as in Formula I. Also, in Structure I-G, $R^{14}$ and $R^{15}$ are each independently selected from the group consisting of hydrogen, halogen, hydroxyl, cyano, nitro, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, substituted or unsubstituted carboxyl, or substituted or unsubstituted sulfonyl. Optionally, $R^{14}$ and $R^{15}$ are hydrogen.

A class of efflux pump inhibitors useful in the methods described herein comprises compounds represented by Formula II:

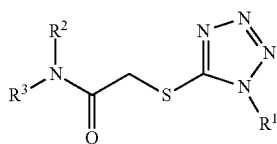

or a pharmaceutically acceptable salt or prodrug thereof.

In Formula II, $R^1$, $R^2$, and $R^3$ are each independently selected from hydrogen, substituted alkyl, substituted alkenyl, substituted alkynyl, substituted or unsubstituted aryl, or substituted or unsubstituted heteroaryl. Optionally, $R^1$ is tert-butyl. Optionally, $R^2$ is hydrogen. Optionally, $R^3$ is tert-butyl. In some examples of Formula II, $R^2$ and $R^3$ are not simultaneously hydrogen. Optionally, $R^1$ and $R^2$ are identical.

In some examples of Formula II, $R^3$ is hydrogen to provide Structure II-A:

Structure II-A

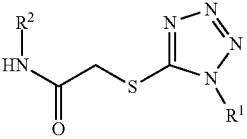

Examples of efflux pump inhibitors useful in the methods described herein include the following compounds:

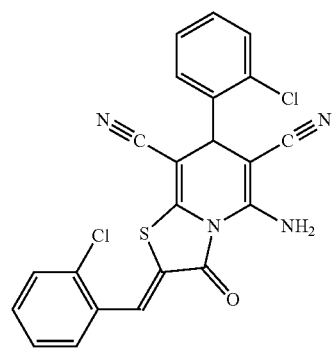

ST006953

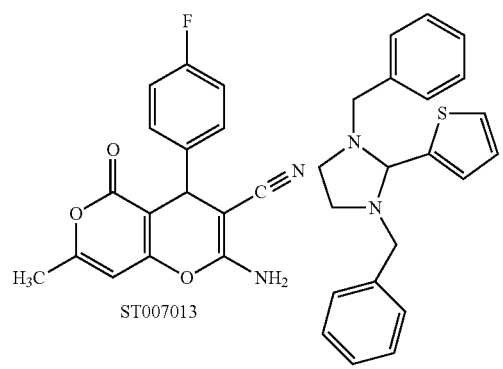

ST007013

ST007852

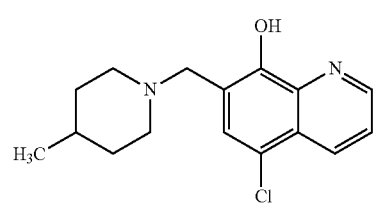

ST007924

-continued
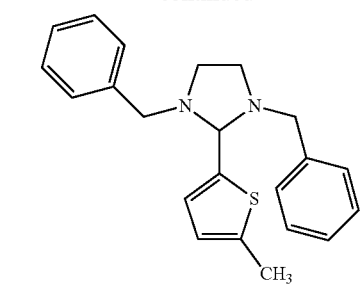
ST008277
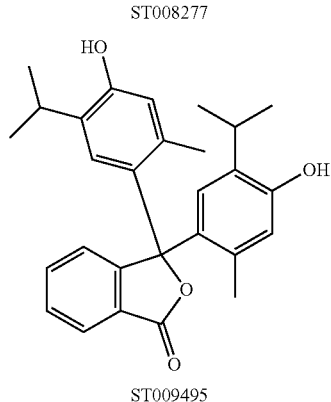
ST009495
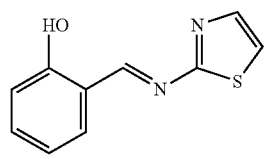
ST009531
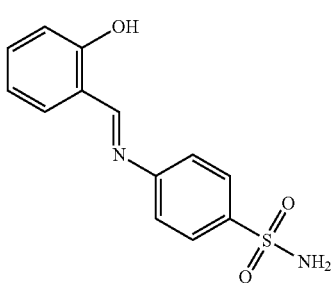
ST009655
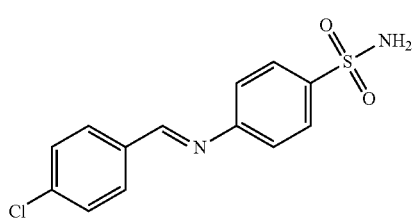
ST009675 (ABEPI1)
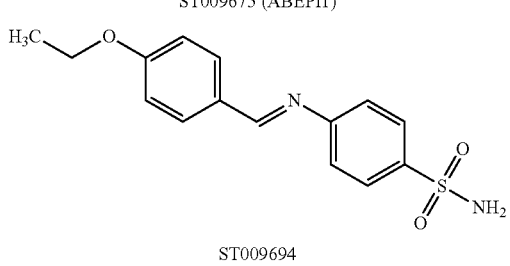
ST009694
-continued
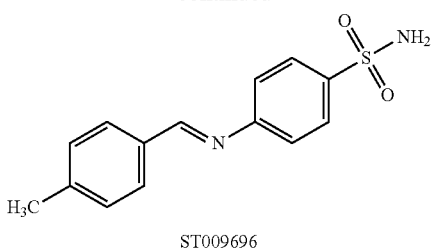
ST009696
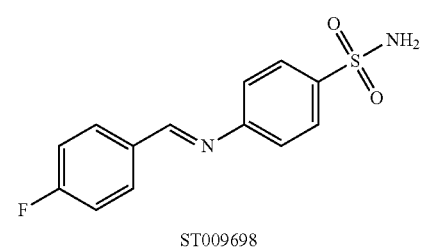
ST009698
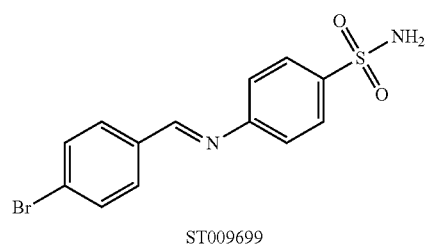
ST009699
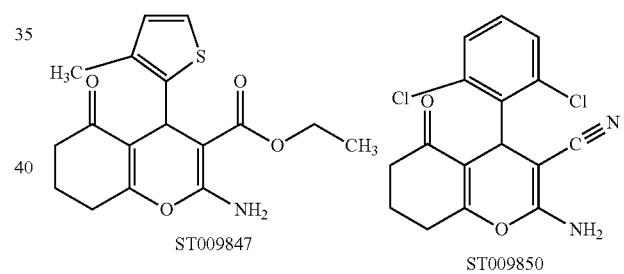
ST009847  ST009850
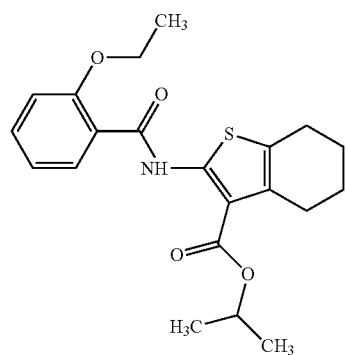
ST009896
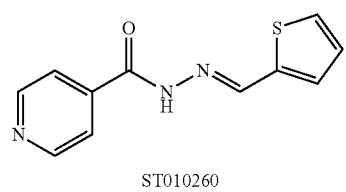
ST010260

-continued
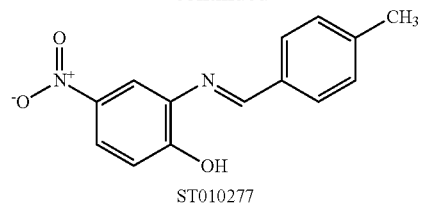
ST010277
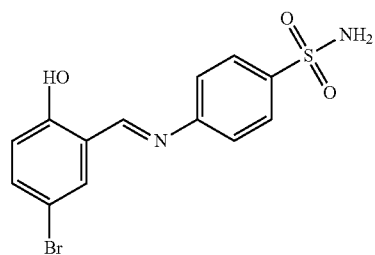
ST010344
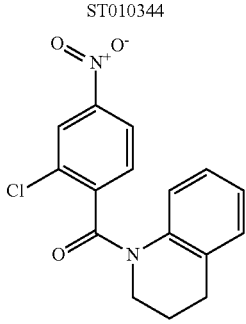
ST011123
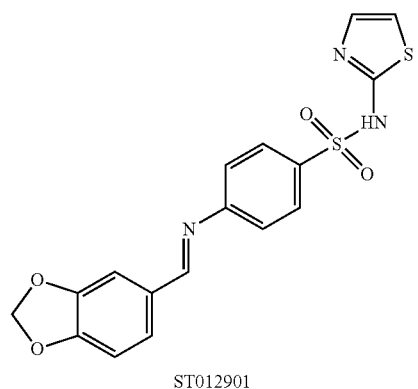
ST012901
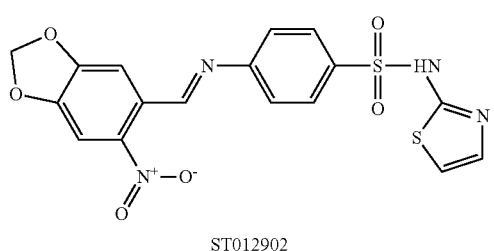
ST012902
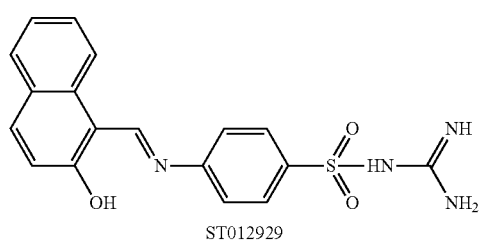
ST012929
-continued
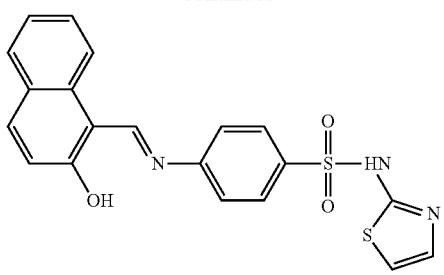
ST012934
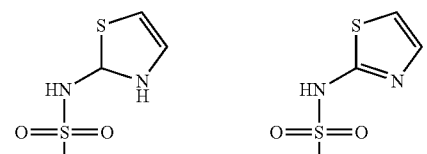
ST012941    ST012955
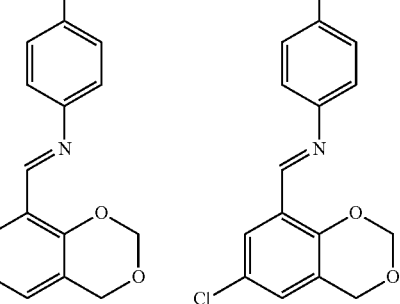
ST012961
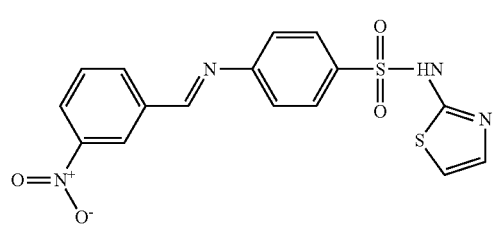
ST012963
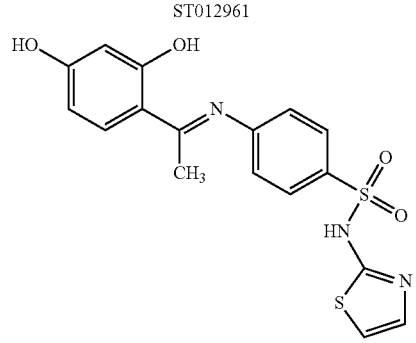
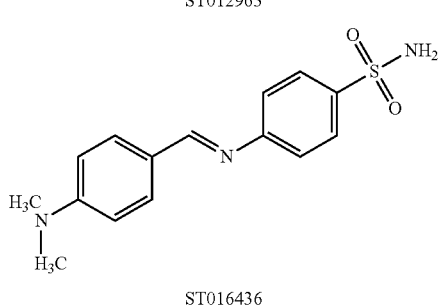
ST016436

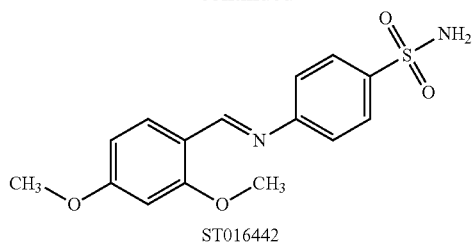
ST016442
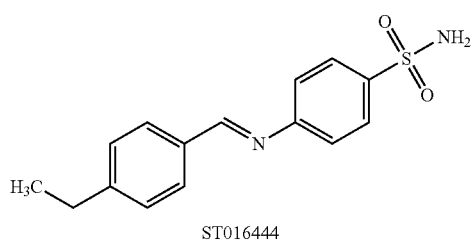
ST016443
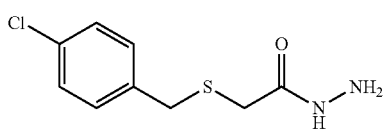
ST016444
ST026450
ST026465
ST020959
ST020992
ST024775
ST025773
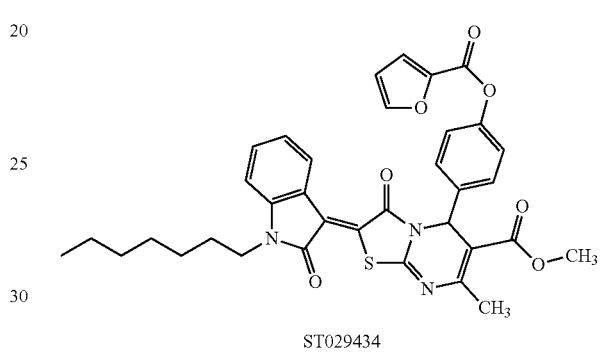
ST029434
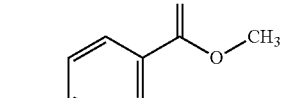
ST0131144
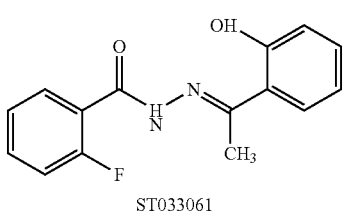
ST033061
ST033063

-continued
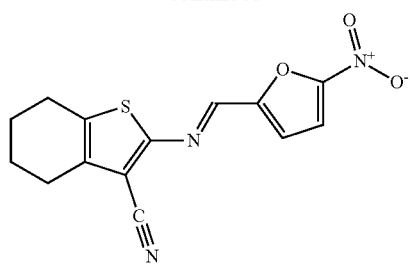
ST033065
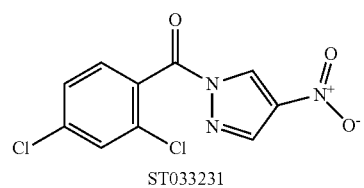
ST033231
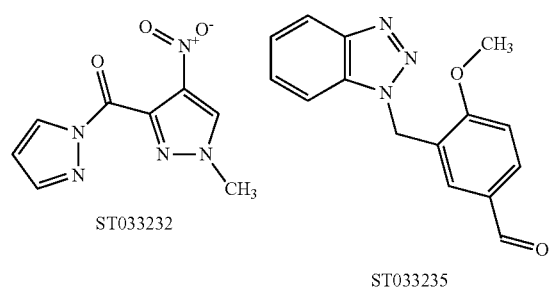
ST033232    ST033235
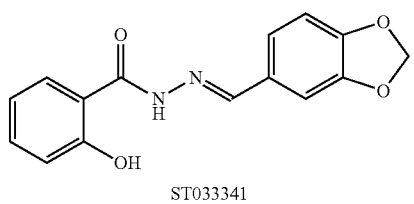
ST033341
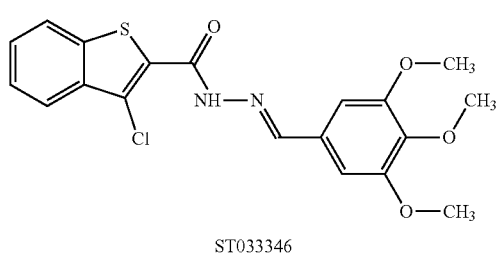
ST033346
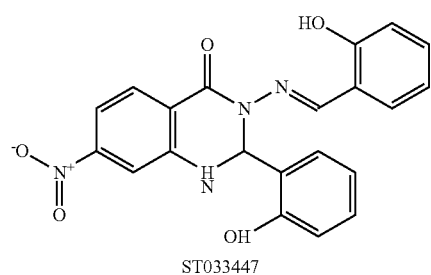
ST033447
-continued
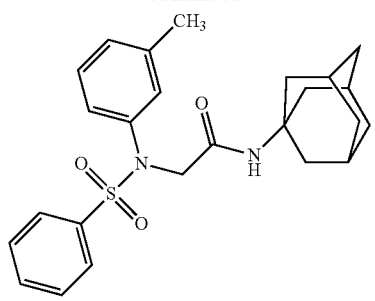
ST034012
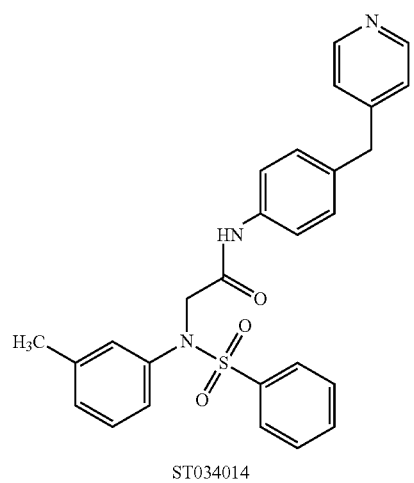
ST034014
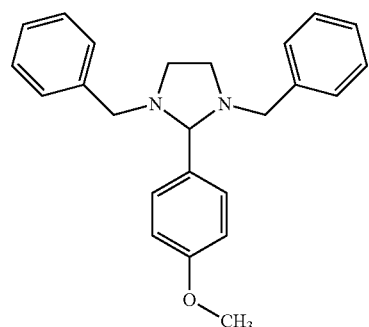
ST036291
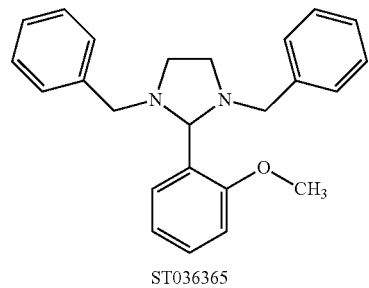
ST036365
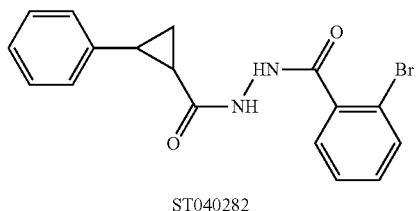
ST040282

-continued
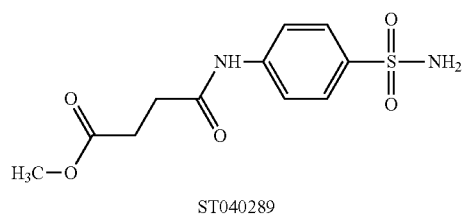
ST040289
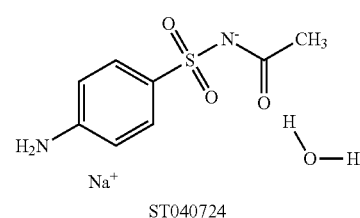
ST040724
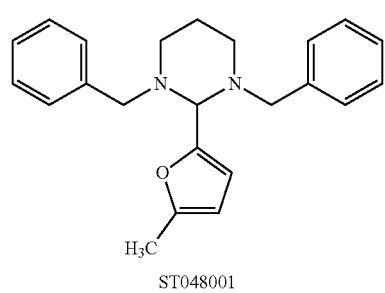
ST048001
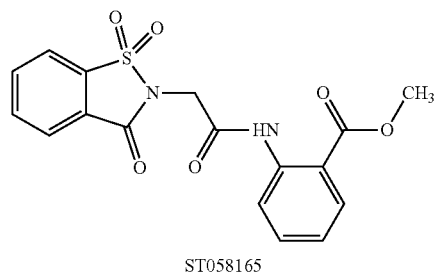
ST058165
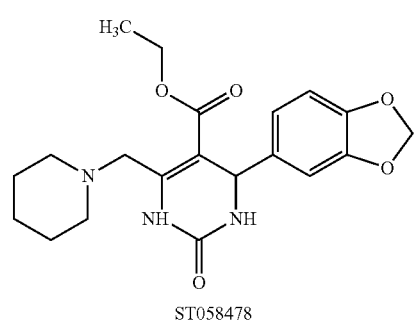
ST058478
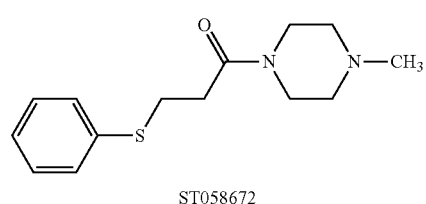
ST058672
-continued
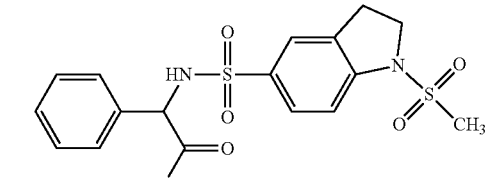
ST058811
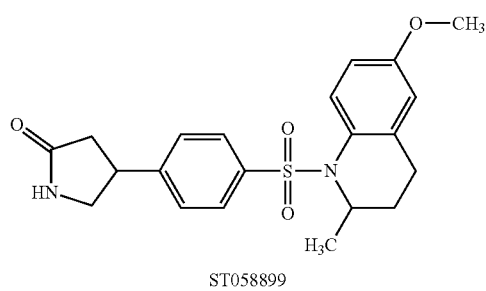
ST058899
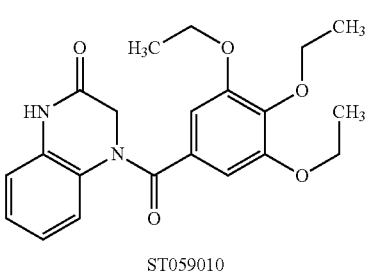
ST059010
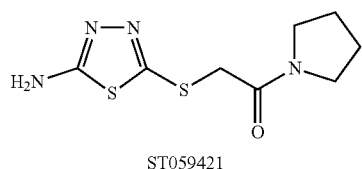
ST059421
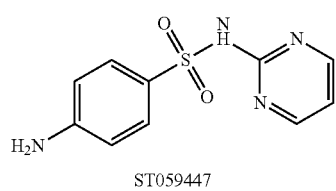
ST059447
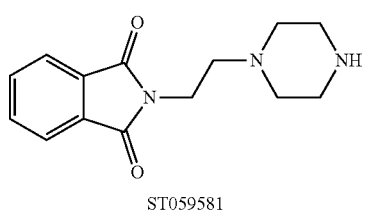
ST059581

-continued

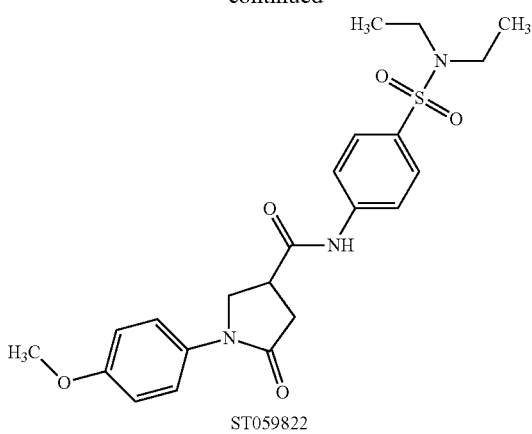
ST059822

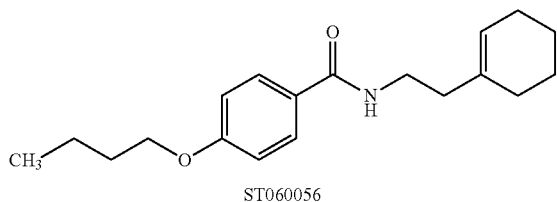
ST060053

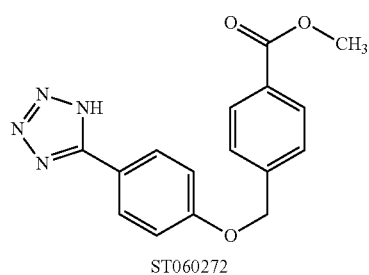
ST060056

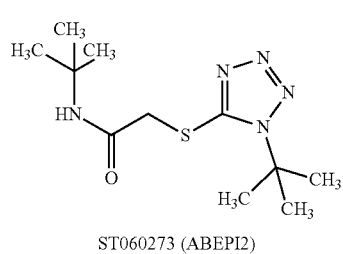
ST060272

ST060273 (ABEPI2)

-continued

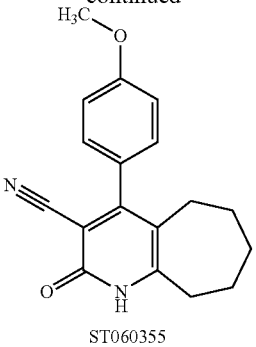
ST060355

Optionally, the efflux pump inhibitor is ST009675 (ABEPI1) or ST060273 (ABEPI2). Optionally, the efflux pump inhibitor is not ST009655, ST009694, ST009699, ST009696, ST009698, ST010277, ST010344, ST012901, ST012902, ST012929, ST012934, ST012941, ST012955, ST012961, ST012963, ST016436, ST016442, ST016443, ST016444, ST009531, ST006953, ST007013, ST007852, ST007924, ST008277, ST009495, ST009847, ST060355, ST009850, ST009896, ST010260, ST011123, ST020959, ST020992, ST024775, ST025773, ST026450, ST026465, ST029434, ST031144, ST033061, ST033063, ST033065, ST033231, ST033232, ST033235, ST033341, ST033346, ST033447, ST034012, ST034014, ST036291, ST036365, ST040282, ST040289, ST040724, ST048001, ST058165, ST058478, ST058672, ST058811, ST058899, ST059010, ST059421, ST059447, ST059581, ST059822, ST060053, ST060056, or ST060272.

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane (—$(CH_2)_9$—$CH_3$).

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, suspensions, ointments, gels, creams, or solutions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing one or more of the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of one or more of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain one or more additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the one or more compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component(s).

Dosage forms for topical administration of the one or more compounds described herein or derivatives thereof include ointments, powders, sprays, inhalants, gels, creams, and solutions. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound or compounds employed, the metabolic stability and length of action of the compound(s); the species, age, body weight, general health, sex and diet of the subject; the mode and time of administration; rate of excretion; drug combination; and severity of the particular condition.

III. Methods of Making the Compounds

The compounds described herein can be prepared in a variety of ways known in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, and the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety. The synthesis and subsequent testing of various compounds as described herein to determine efficacy is contemplated.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Optionally, the compounds described herein can be obtained from commercial sources, including, for example, TimTec (Newark, Del.).

IV. Methods of Use

Provided herein are methods to treat, prevent, or ameliorate microbial infections in a subject. The methods include administering to the subject an effective amount of an efflux pump inhibitor as described herein and an antimicrobial agent. The compounds and compositions described herein or pharmaceutically acceptable salts thereof are useful for treating microbial infections in humans, e.g., pediatric and geriatric populations, and in animals, e.g., veterinary applications. Microbial infections include, for example, bacterial infections and fungal infections. In some examples, the microbial infection is a bacterial infection. Optionally, the bacterial infection is a Gram-negative bacterial infection, such as an *Acinetobacter* infection (e.g., an *Acinetobacter baumannii* infection), a *Pseudomonas* infection (e.g., a *Pseudomonas aeruginosa* infection), a *Klebsiella* infection, an *Escherichia* infection, a *Salmonella* infection, a *Yersinia* infection, a *Shigella* infection, a *Proteus* infection, an *Enterobacter* infection, a *Serratia* infection, or a *Citrobacter* infection. In some examples, the microbial infection is a Gram-positive bacterial infection, such as a *Bacillus* infection, a *Listeria* infection, a *Staphylococcus* infection, a *Streptococcus* infection, an *Enterococcus* infection, or a *Clostridium* infection.

The methods of treating, preventing, or ameliorating microbial infections in a subject can further include selecting a subject infected with a microbe that is resistant to the antimicrobial agent or selecting a subject infected with a microbe that is capable of developing resistance to the antimicrobial agent. Optionally, the resistance is mediated by an efflux pump. The efflux inhibitors described herein can increase the susceptibility of the microbe to the antimicrobial agent. Optionally, the efflux inhibitors described herein can enhance the antimicrobial activity of the antimicrobial agent against the microbe.

These methods can further include treatment with one or more additional therapeutic agents (e.g., an antibiotic). The one or more additional agents and the compounds and compositions or pharmaceutically acceptable salts thereof as described herein can be administered in any order, including simultaneous administration, as well as sequentially (e.g., temporally spaced order of up to several days apart). The methods may also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein may be by the same or different routes. When treating with one or more additional agents, the compounds and compositions or pharmaceutically acceptable salts thereof as described herein can be combined into a pharmaceutical composition that includes the one or more additional agents. For example, the compounds and compositions or pharmaceutically acceptable salts thereof as described herein can be combined into a pharmaceutical composition with an antibiotic. Suitable antibiotics can include any antibiotic effective for treating a bacterial infection and include, for example, tetracyclines (e.g., minocycline), quinolones (e.g., ciprofloxacin, levofloxacin, and nalidixic acid), aminoglycosides (e.g., amikacin, gentamycin, kanamycin, and tobramycin), carbapenems (e.g., meropenem), cephalosporins (e.g., ceftriaxone), macrolides (e.g., erythromycin), polypeptides (e.g., colistin and polymxin B), sulfonamides (e.g., sulfamethoxazole), glycylcyclines (e.g., tigecycline), beta lactams (e.g., penams), lipopeptides (e.g., daptomycin), oxazolidinones (e.g., linezolid), and trimethoprim.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of a microbial infection), during early onset (e.g., upon initial signs and symptoms of a microbial infection), after an established microbial infection, or even after resistance to antibiotic occurs. Prophylactic administration can occur for several days to years prior to the manifestation of symptoms of an infection. Therapeutic treatment involves administering to a subject a therapeutically effective amount of the compound(s) and composition(s) or pharmaceutically acceptable salts thereof as described herein after a microbial infection is diagnosed.

Also provided herein are methods of inhibiting an efflux pump in a cell, including eukaryotic and prokaryotic cells. Suitable classes of classes of prokaryotic efflux pumps include major facilitator superfamily, ATP-binding cassette (ABC) superfamily, small multidrug resistance (SMR) family, resistance-nodulation cell division (RND) superfamily, multi-antimicrobial extension (MATE), and drug metabolite transporter (DMT) superfamily. Suitable classes of eukaryotic efflux pump include monocarboxylate transporter (MCT), multidrug resistance proteins, multidrug resistance-associated proteins, peptide transporters (PEPTs), and Na+ phosphate transporters (NPTs).

The methods of inhibiting an efflux pump in a cell can include contacting the cell with an effective amount of an efflux pump inhibitor as described herein. The effective amount of the efflux pump inhibitor can be the amount that inhibits an efflux pump in the cell. Optionally, the cell can be a microbial cell. Optionally, the microbial cell can be a bacterial cell. Optionally, the bacterial cell is a gram-negative bacterial cell. Optionally, the gram-negative bacterial cell is an *Acinetobacter* bacterial cell (e.g., an *Acinetobacter baumannii* bacterial cell), a *Pseudomonas* bacterial cell (e.g., a *Pseudomonas aeruginosa* bacterial cell), a *Klebsiella* bacterial cell, an *Escherichia* bacterial cell, a *Salmonella* bacterial cell, a *Yersinia* bacterial cell, a *Shigella* bacterial cell, a *Proteus* bacterial cell, an *Enterobacter* bacterial cell, a *Serratia* bacterial cell, or a *Citrobacter* bacterial cell. Optionally, the bacterial cell is a gram-positive bacterial cell. Optionally, the gram-positive bacterial cell is a *Bacillus* bacterial cell, a *Listeria* bacterial cell, a *Staphylococcus* bacterial cell, a *Streptococcus* bacterial cell, an *Enterococcus* bacterial cell, or a *Clostridium* bacterial cell. The contacting can be in vivo (e.g., in a human subject) or in vitro.

V. Kits

Also provided herein are kits for treating or preventing microbial infections (e.g., bacterial infections) in a subject. A kit can include any of the compounds (alone or in combination) or one or more compositions described herein and one or more additional agents, such as an antibiotic agent. For example, a kit can include a compound as described herein and an antibiotic agent such as tetracyclines (e.g., minocycline), quinolones (e.g., ciprofloxacin, levofloxacin, and nalidixic acid), aminoglycosides (e.g., amikacin, gentamycin, kanamycin, and tobramycin), a carbapenem (e.g., meropenem), a cephalosporin (e.g., ceftriaxone), a macrolide (e.g., erythromycin), polypeptides (e.g., colistin and polymxin B), a sulfonamide (e.g., sulfamethoxazole), glycylcycline (e.g., tigecycline), and trimethoprim. A kit can further include an oral formulation of any of the compounds or compositions described herein. A kit can additionally include directions for use of the kit (e.g., instructions for treating a subject), one or more containers (for the compound(s), composition(s), or additional agent(s)), a means for administering the compounds or compositions, and/or a carrier.

As used herein the terms treatment, treat, or treating refer to reducing one or more symptoms of an infection, a disease, or a condition. Thus in the disclosed method, treatment can refer to a reduction by 10%, 20%, 30%, 40%, 50%, 60%, 70%, 80%, 90%, 100%, or any percent reduction in between 10% and 100% in the severity of one or more symptoms of the infection, disease, or condition. For example, a method for treating an infection is considered to be a treatment if there is a 10% reduction in one or more symptoms or signs of the infection in a subject as compared to a control. As used herein, control refers to the untreated infection. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection, disease, condition, or symptoms of the infection, disease, or condition.

As used herein, the terms prevent, preventing, and prevention of an infection, disease, or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater, or any percent change in between 10% and greater than about 90% or greater, as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

The examples below are intended to further illustrate certain aspects of the methods and compositions described herein, and are not intended to limit the scope of the claims.

EXAMPLES

Bacterial Strains and Growth Conditions:

*A. baumannii* strains 98-37-02, 98-37-05, 98-37-09, and 07-09-54 are clinical isolates obtained from the Centers for Disease Control and Prevention. *Pseudomonas aeruginosa* strain PA01 and *Klebsiella pneumonaie* strain CKP4 are common laboratory strains. All strains were grown in either Luria-Bertani (LB) medium (Becton Dickinson, Franklin Lakes, N.J.) or 100% human serum (MP Biomedicals, Solon, Ohio). Where indicated, LB or serum was supplemented with kanamycin (50 μg ml$^{-1}$, Thermo Fisher, Waltham, Mass.), and/or the indicated concentration of minocycline (Sigma-Aldrich, Saint Louis, Mo.), ciprofloxacin (Sigma Aldrich), meropenem (LKT laboratories, Minneapolis-St. Paul, Mo.), or tigecycline (Pfizer, Groton, Conn.).

Example 1

Antibiotic Susceptibility Assays

Antibiotic efflux pumps have been found to contribute to bacterial resistance to virtually every currently available antibiotic. Ten *A. baumannii* antibiotic efflux systems have been characterized to date. It has been shown that *A. baumannii* growth in human serum, a biologically relevant medium, induces the expression of twenty-two previously uncharacterized drug efflux pump-associated genes and that their expression corresponds to efflux-mediated tolerance to the antibiotic minocycline at levels correlating to patient serum levels during treatment. As a means to evaluate this phenomenon further, it was herein assessed whether *A. baumannii* growth in serum elicits drug-efflux mediated tolerance to other tetracyclines, quinolones (ciprofloxacin, levofloxacin, and nalidixic acid), aminoglycosides (amikacin, gentamycin, and kanamycin), a carbapenem (meropenem), a cephalosporin (ceftriaxone), a macrolide (erythromycin), polypeptides (colistin and polymxin B), a sulfonamide (sulfamethoxazole), glycylcycline (tigecycline), and trimethoprim.

The antibiotic susceptibility of *A. baumannii* and *Pseudomonas aeruginosa* grown in either LB medium or 100% human serum was measured according to the method described below. Briefly, the indicated bacterial species/strain was grown overnight in LB medium, diluted into fresh medium (1:100 dilution) and grown to mid-exponential phase (OD$_{600nm}$=0.4 to 0.5) at 37° C. with aeration. A total of 1×10⁵ colony forming units (CFU) were transferred to individual wells of a 96-well round bottom plate containing 100 µL of LB or 100% human serum supplemented with 2-fold increasing concentrations (0 to 2 µg mL$^{-1}$) of minocycline, amikacin, gentamicin, kanamycin, meropenem, ceftriaxone, erythromycin, colistin, polymyxin B, ciprofloxacin, levofloxacin, nalidixic acid, sulfamethoxazole, trimethoprim, tigecycline or 0 to 16 µg mL$^{-1}$ tetracycline and incubated at 37° C. for 48 hours. To quantify the antimicrobial effects of each antibiotic toward bacteria grown in LB or serum, well constitutes were serially diluted in PBS and plated on LB agar to enumerate the CFU mL$^{-1}$. Where indicated, antimicrobial susceptibility assays were also performed in the presence of 50 µg mL$^{-1}$ the efflux pump inhibitors, verapamil, reserpine, phenylalanine arginine beta naphthylamide (PAβN) or the putative efflux inhibitors ABEPI1 and ABEPI2, to measure the contribution(s) of antibiotic efflux pumps to antibiotic tolerance or the ability of putative efflux inhibitors to potentiate the antimicrobial activity of the indicated antibiotic, respectively.

As shown in FIG. 1A, in comparison to growth in LB, *A. baumannii* strain 98-37-09 grown in human serum were significantly (P<0.001) less susceptible to ciprofloxacin at concentrations ≤1 µg ml$^{-1}$. Ciprofloxacin susceptibility could be restored to cells grown in serum supplemented with the known efflux pump inhibitor, reserpine, showing that the organism's serum associated-ciprofloxacin tolerance was efflux mediated as opposed to antibiotic sequestration and/or inactivation by serum components. Likewise, *A. baumannii* grown in human serum displayed efflux-mediated tolerance to the tetracycline at antibiotic concentrations ≥2 µg ml$^{-1}$ (FIG. 1B). More specifically, treatment of LB grown *A. baumannii* with 4-16 µg ml$^{-1}$ tetracycline reduced cell viability to undetectable levels (<1×10$^1$ colony forming units; cfu), whereas cells grown in serum displayed considerable antibiotic tolerance, equaling between 1×10⁶ and 1×10⁴ cfu. Serum grown *A. baumannii* tetracycline susceptibility was partially restored in the presence of the drug efflux pump inhibitor PAβN, showing that efflux pumps, in part, modulate the organism's tetracycline tolerance during serum growth. Similar phenotypes were observed for representatives of three of eleven previously characterized *A. baumannii* lineages evaluated, indicating that serum-associated efflux pump mediated minocycline and ciprofloxacin tolerance is a semi-conserved *A. baumannii* response that is presumably dependent on the genetic composition of the organism evaluated. Further, while significant differences were not observed between the susceptibility of serum and LB grown 98-37-09 cells to other classes of antibiotics tested, during the course of investigations, strains representing seven of the eleven other lineages tested displayed, albeit varying, but significantly increased efflux-mediated tolerance to the antibiotic tigecycline during serum growth (representative results shown in FIG. 1C). As an example, tigecycline displayed clear antimicrobial activity toward *A. baumannii* strain 01-12-05 during growth in LB medium at concentrations ≥1 µg ml$^{-1}$, but the strain appeared to be highly-resistant to the antibiotic during growth in serum. Susceptibility could be partially restored by addition of the efflux pump inhibitor, reserpine, showing that serum-associated efflux pump activity(ies) at least in part contributes to the strains ability to tolerate tigecycline during growth in serum.

The observed serum-dependent efflux-pump mediated antibiotic tolerance can, in part, account for the clinical failure of antibiotics toward clinically defined susceptible *A. baumannii* strains; during adaptation to host-associated environmental conditions, such as serum, the organism induces efflux pumps that allow clinically defined antibiotic susceptible organisms to tolerate antibiotic challenge in vivo. Accordingly, adjunctive therapy with corresponding efflux-pump inhibitors provides a valuable strategy to limit antibiotic tolerance within the host and, consequently, poses as an attractive therapeutic approach for both current and future antibiotics.

Example 2

High Throughput Screen for *A. baumannii* Serum-dependent Antibiotic Efflux Pump Inhibitors The TimTec ActiProbe-25K diversity-set and Natural Product compound libraries (29,900 compounds total; TimTec, Newark, Del.) were initially screened for putative efflux pump inhibitors by identifying compounds that potentiated the antimicrobial property of a sub-inhibitory concentration of minocycline toward *A. baumannii* grown in human serum. To do so, *A. baumannii* strain 98-37-09 was grown for 16 hours in LB medium at 37° C. on a rotary shaker at 225 rpm. Approximately 1×10⁵ CFU were then transferred to individual wells of a 96-well round-bottom plate (Corning Costar, Tewksbury, Mass.) containing 100 µL of human serum supplemented with of minocycline (0.5 µg mL$^{-1}$; 0.5× minimum inhibitory concentration in serum) and individual members of the Timtec ActiProbe or Natural product library (50 µM). Plates were then incubated at 37° C. for 48 hours. Growth was measured as a function of turbidity. Putative efflux pump inhibitors were identified as compounds that inhibited *A. baumannii* growth in human serum containing minocycline and were subsequently retested in triplicate, as indicated above. Untreated *A. baumannii* grown in serum supplemented with minocycline+/−PAβN served as positive and negative controls, respectively. Most compounds (99.6%; 29,806 compounds) did not affect the organism's growth, whereas 94 compounds (0.4%) inhibited the strain's ability to grow in serum supplemented with minocycline. Repeat testing in which well constituents were serial diluted and plated on LB agar plates validated that 85 compounds did indeed limit *A. baumannii* growth in serum supplemented with minocycline, reducing the number of viable colony forming units between 2-6 log cfu in comparison to minocycline alone treated cells.

To distinguish compounds with inherent antimicrobial properties from putative efflux pump inhibitors, each compound was subsequently evaluated for antimicrobial activity toward *A. baumannii* in serum or LB in the absence of minocycline. To do so, 1×10⁵ CFU of *A. baumannii* strain 98-37-09 were added to individual wells of a microtiter plate containing 100 µL 100% human serum supplemented with increasing concentrations of the test compound (0 to 128 µg mL$^{-1}$) and incubated at 37° C. for 48 hours. Twelve of the 85 compounds tested (12.7%) exhibited antimicrobial activity toward *A. baumannii* grown in serum and/or LB in the absence of minocycline and may represent novel antimicrobial agents. The remaining 73 compounds did not display antimicrobial activity in the absence of minocycline, suggesting that a subset of these compounds may represent efflux pump inhibitors that potentiate the antimicrobial activity of minocycline toward serum grown *A. baumannii*. Compounds that displayed antimicrobial activity were archived, whereas those that did not exhibit direct antibacterial activity were considered putative efflux inhibitors and the minimum effective concentration (MEC) at which they potentiated the antimicrobial activity of minocycline toward serum grown *A. baumannii* was determined.

For MEC determination, individual wells of 96-well round-bottom plates containing 100% human supplemented with 0.5×MIC minocycline (0.5 μg mL$^{-1}$) and increasing concentrations of test compound (0 to 128 g mL$^{-1}$) were inoculated with approximately 1×10$^5$ CFU of *A. baumannii* strain 98-37-09 and incubated for 48 hr at 37° C. The MEC was defined as the lowest concentration of test compound required to inhibit the growth of *A. baumannii* in serum in the presence of 0.5 μg ml$^{-1}$ minocycline. Plating confirmed that addition of 1×MEC of each compound elicited ≥1.9-log reduction in *A. baumannii* cells grown in serum supplemented with minocycline alone (see Table 1).

TABLE 1

| ID | MEC | Log-reduction Colony Forming Units (ml$^{-1}$) | Minocylcine Per Cell (femtomoles cell$^{-1}$) | % Viability | Potentiate Ciprofloxacin *A. baumannii* | Potentiate Ciprofloxacin *P. aeruginosa* |
|---|---|---|---|---|---|---|
| ST006953 | 4 ug/mL | 2.71 | 4.310000E−08 | | | |
| ST007013 | 4 ug/mL | 1.95 | 5.000000E−04 | 80.9 | No | |
| ST007852 | 4 ug/mL | 4.21 | 5.900000E−05 | 65.77 | | |
| ST007924 | 4 ug/mL | 2.42 | 5.120000E−05 | 67.45 | | |
| ST008277 | 4 ug/mL | 5.19 | 4.410000E−08 | | | |
| ST009495 | 2 ug/mL | 2.23 | 4.700000E−08 | | | |
| ST009531 | 2 ug/mL | 2.77 | 5.880000E−09 | | | |
| ST009655 | 2 ug/mL | 6.67 | 2.610000E−07 | | | |
| ST009675 | 2 ug/mL | 6.73 | 5.880000E−04 | 96.6 | Yes (2.28) | Yes (>8.0) |
| ST009694 | 4 ug/mL | 6.24 | 6.800000E−07 | 74.6 | | |
| ST009696 | 4 ug/mL | 5.67 | 8.200000E−09 | | | |
| ST009698 | 64 ug/mL | 6.45 | 1.520000E−05 | 73.56 | | |
| ST009699 | 2 ug/mL | 6.84 | 1.150000E−04 | 70.45 | | |
| ST009847 | 2 ug/mL | 4.97 | 2.540000E−07 | | | |
| ST009850 | 2 ug/mL | 2.47 | 7.250000E−08 | | | |
| ST009896 | 2 ug/mL | 2.45 | 3.990000E−05 | 73.54 | | |
| ST010260 | 16 ug/mL | 2.66 | 3.270000E−08 | | | |
| ST010277 | 32 ug/mL | 7.33 | 1.150000E−05 | 82.4 | No | |
| ST010344 | 32 ug/mL | 5.29 | 2.980000E−08 | | | |
| ST011123 | 32 ug/mL | 2.83 | 1.190000E−05 | 67.89 | | |
| ST012901 | 2 ug/mL | 2.66 | 4.160000E−09 | | | |
| ST012902 | 2 ug/mL | 3.71 | 1.100000E−05 | 55.1 | | |
| ST012929 | 32 ug/mL | 4.64 | 2.740000E−08 | | | |
| ST012934 | 32 ug/mL | 4.42 | 2.280000E−08 | | | |
| ST012941 | 64 ug/mL | 6.23 | 8.120000E−09 | | | |
| ST012955 | 32 ug/mL | 4.42 | 1.040000E−08 | | | |
| ST012961 | 32 ug/mL | 6.23 | 1.130000E−04 | 59.32 | | |
| ST012963 | 32 ug/mL | 3.90 | 3.230000E−08 | | | |
| ST016436 | 16 ug/mL | 4.98 | 5.380000E−05 | 55.73 | | |
| ST016442 | 2 ug/mL | 3.88 | 1.960000E−04 | 53.43 | | |
| ST016443 | 2 ug/mL | 2.00 | 4.400000E−04 | 57.49 | | |
| ST016444 | 16 ug/mL | 4.86 | 2.020000E−05 | 53.92 | | |
| ST020959 | 2 ug/mL | 6.90 | 1.270000E−04 | 51.04 | | |
| ST020992 | 2 ug/mL | 7.43 | 1.530000E−07 | | | |
| ST024775 | 16 ug/mL | 4.84 | 1.720000E−05 | 41.62 | | |
| ST025773 | 32 ug/mL | 8.00 | 1.040000E−07 | | | |
| ST026450 | 32 ug/mL | 5.37 | 2.350000E−06 | 100 | No | |
| ST026465 | 32 ug/mL | 6.36 | 3.820000E−04 | 100 | No | |
| ST029434 | 64 ug/mL | 3.02 | 1.730000E−08 | | | |
| ST031144 | 2 ug/mL | 8.00 | 2.090000E+03 | 63.7 | | |
| ST033061 | 2 ug/mL | 2.18 | 1.960000E−04 | 77.58 | No | |
| ST033063 | 2 ug/mL | 1.93 | 5.840000E−08 | | | |
| ST033065 | 2 ug/mL | 2.44 | 2.060000E−05 | 75.6 | No | |
| ST033231 | 32 ug/mL | 1.91 | 3.420000E−06 | 70.87 | | |
| ST033232 | 16 ug/mL | 2.32 | 2.320000E−06 | 77.75 | No | |
| ST033235 | 32 ug/mL | 2.21 | 6.651840E−08 | | | |
| ST033341 | 2 ug/mL | 2.42 | 3.390000E−05 | 75.88 | No | |
| ST033346 | 2 ug/mL | 2.00 | 3.615000E−07 | 74.67 | | |
| ST033447 | 32 ug/mL | 1.92 | 3.680000E−06 | 74.39 | | |
| ST034012 | 2 ug/mL | 2.00 | 1.550000E−07 | | | |
| ST034014 | 2 ug/mL | 2.37 | 5.460000E−04 | 84.27 | No | |
| ST036291 | 2 ug/mL | 3.31 | 5.500000E−05 | 75.74 | No | |
| ST036365 | 4 ug/mL | 3.50 | 3.590000E−08 | | | |
| ST040282 | 4 ug/mL | 2.25 | 3.050000E−06 | 85.04 | No | |
| ST040289 | 4 ug/mL | 4.32 | 8.380000E−04 | 78.8 | No | |
| ST040724 | 64 ug/mL | 4.08 | 1.450000E−04 | 82.42 | No | |
| ST048001 | 32 ug/mL | 7.06 | 1.990000E−04 | 82.72 | No | |
| ST058165 | 32 ug/mL | 6.27 | 1.110000E−04 | 76.9 | Yes (1.53) | No |
| ST058478 | 64 ug/mL | 6.33 | 1.520000E−07 | | | |
| ST058672 | 4 ug/mL | 5.97 | 3.200000E−07 | | | |
| ST058811 | 4 ug/mL | 6.17 | 2.480000E−07 | | | |
| ST058899 | 64 ug/mL | 6.21 | 1.080000E−04 | 80.69 | No | |

TABLE 1-continued

| ID | MEC | Log-reduction Colony Forming Units (ml$^{-1}$) | Minocylcine Per Cell (femtomoles cell$^{-1}$) | % Viability | Potentiate Ciprofloxacin A. baumannii | P. aeruginosa |
|---|---|---|---|---|---|---|
| ST059010 | 32 ug/mL | 6.11 | 3.780000E−08 | | | |
| ST059421 | 4 ug/mL | 6.31 | 1.270000E−07 | | | |
| ST059447 | 4 ug/mL | 5.74 | 4.520000E−05 | 76.78 | No | |
| ST059581 | 32 ug/mL | 6.12 | 5.640000E−05 | 84.56 | No | |
| ST059822 | 4 ug/mL | 6.23 | 1.360000E−07 | | | |
| ST060053 | 4 ug/mL | 4.94 | 1.780000E−04 | 76.11 | No | |
| ST060056 | 4 ug/mL | 5.38 | 4.220000E−08 | | | |
| ST060272 | 32 ug/mL | 6.90 | 3.670000E−07 | 85.35 | No | |
| ST060273 | 32 ug/mL | 6.53 | 6.840000E−06 | 90.1 | Yes (4.36) | Yes (>8.0) |
| ST060355 | 32 ug/mL | 6.94 | 1.230000E−08 | | | |

Example 3

Cellular Accumulation of Minocycline

High pressure liquid chromatography and triple-quadrupole mass spectrometry were used to measure the *A. baumannii* intracellular levels of minocycline during growth in human serum in the absence and presence of each putative efflux pump inhibitor. To do so, *A. baumannii* strain 98-37-09 was grown in 5 mL of 100% human serum supplemented with 0.5 µg mL$^{-1}$ minocycline, in the absence and presence of 0.5×MEC each putative efflux pump inhibitor (test compound) or the known efflux pump inhibitor, verapamil. Cultures were incubated for 48 hours with shaking, at which point an aliquot was removed, serially diluted, and plated to determine the number of viable CFU per mixture. The remainder of the cells were pelleted by centrifugation at 900×g at 4° C., washed twice in PBS, mechanically lysed with a FastPrep cell disrupter (MP Biomedicals, Santa Ana, Calif.) for 20 seconds at 5 m s$^{-1}$ and the cellular debris was pelleted via centrifugation at 900×g and 4° C. The amount of minocycline present within the supernatant of ruptured cells was measured. Briefly, doxycycline (0.5 µg mL$^{-1}$) was first added to each supernatant to serve as an internal control to account for sample-to-sample preparation variability. The supernatant was then combined with acetonitrile (ACN) at a 1:10 ratio and centrifuged at 16,000×g, at 4° C., to collect minocycline and doxycycline. Supernatants were discarded and residual liquid was evaporated in a speed vacuum for 2 hours at 8,000×g. To quantify the amount of antibiotics retained, sample materials were suspended in 50% acetonitrile, filtered through a 0.2 µm low protein binding hydrophilic membrane (Millipore, Billerica, Mass.) then separated on Shimadzu high performance liquid chromatography instrument (Fisher Scientific) using a BetaBasic C18 reverse phase column (Thermo Scientific). Separation was carried out with two mobile phase solutions consisting of solution (A) water with 0.1% formic acid and solution (B) 100% ACN. The gradient profile of the chromatography runs was as follows: from 0 to 0.1 min 8% solution B, ramp step wise (37% to 60% solution B) from 0.1 to 6.5 min then holding for one minute before ramping down from 60% to 10% from 7.5 to 8 min. This was followed a hold at 10% solution B for one minute. From 10 to 13 min the gradient was ramped to 100% solution B and held until 11.5 minutes and then reduced to 8% solution B and in these conditions for an additional four minutes. The column was equilibrated in 8% solution B at 40° C. and the flow rate was set to 0.2 mL min$^{-1}$. Mass spectrometry analysis of fractions was carried out using a Thermo TSQ Quantum Ultra triple quadrupole mass spectrometer (Fisher Scientific). Data were analyzed using Xcalibur software (Thermo Scientific); the following parameters were used to detect minocycline and the internal control doxycycline: 458.208 m/z→282.971 m/z (collision energy=43, tube lens=119) for minocycline and 445.144 m/z→266.900 m/z (collision energy=39, tube lens=127) for doxycycline. Analysis of the raw data was conducted by using the area under the curve calculations with the Genesis algorithm to determine the concentration in each sample. The difference between the peak intensity and the y intercept of pre-established minocycline and doxycycline standard curves was divided by the slope of the standard curve to quantify the amount of minocycline within each sample. The total concentration of minocycline within each cell was calculated by normalizing to the number of cells within each corresponding culture.

Figure 2:
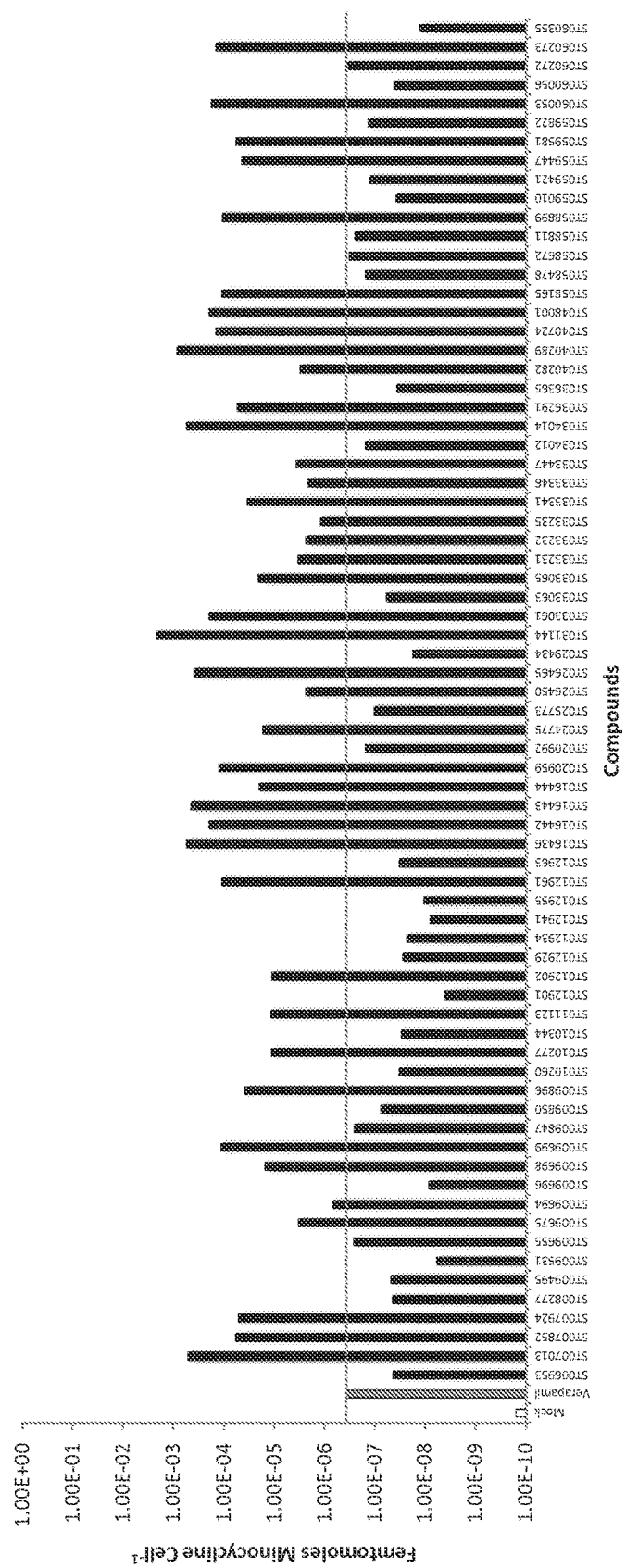
FIG. 2 is a graph showing the concentration of minocycline accumulated per cell in *A. baumannii* strain 98-37-09 grown in human serum supplemented with 0.5 μg ml$^{-1}$ minocycline and either 50 μg ml$^{-1}$ verapamil or 1×MEC of the compounds described herein. The dashed line represents the concentration of minocycline within cells grown in human serum supplemented with minocycline and 50 μg ml$^{-1}$ verapamil.

During growth in serum (efflux active conditions), the cellular minocycline concentration was determined to be 1.58×10$^{-10}$ femtomoles per bacterial cell, whereas addition of the known efflux pump inhibitor, verapamil, increased the cellular concentration nearly 1,000-fold (3.56×10$^{-7}$ femtomoles cell$^{-1}$), indicating that the approach is appropriate to measure efflux-pump dependent cellular antibiotic accumulation. As shown in FIG. 2, while virtually all of the compounds evaluated appeared to induce minocycline accumulation in comparison to mock treated cells, 41 compounds stimulated minocycline accumulation within serum grown *A. baumannii* cells to levels equaling or exceeding that of the known antibiotic efflux pump inhibitor, verapamil, and were considered to be highest priority agents that presumably include efflux inhibitors as well as compounds that lead to antibiotic accumulation via unappreciated means. These 41 compounds were considered putatively clinically valuable agents that potentiate the antimicrobial activity and cellular accumulation of minocycline toward *A. baumannii* in serum and were carried forward for further characterization.

Example 4

Cytotoxicity Assay

To distinguish putatively non-toxic from human cytotoxic compounds, conventional 3-(4,5-dimethylthiazol-2yl)-2,5-diphenyltetrazolium bromide (MTT) cell viability assays (American Type Culture Collection, Manassas, Va.) were performed for each compound of interest at 1× and 4× their MEC. Briefly, human HepG2 cells were grown to approximately 1×10⁶ cells per well in Dulbecco's Modified Eagle Media supplemented with 10% fetal bovine serum (Invitrogen, Carlsbad, Calif.) then treated with 1× or 4× the MEC of the indicated compound alone and in combination with 0.5 µg ml$^{-1}$ minocycline for 24 hours. Cell viability was measured following the addition of the tetrazolium salt (MTT) as per the manufacturer's recommendations; cells challenged with 50 ug ml$^{-1}$ Mitomycin C (Sigma Aldrich) and mock-treated cells served as positive and negative controls, respectively.

As shown in Table 1, 19 (46.3%) of the compounds tested elicited significant toxicity toward HepG2 cells, which was defined has <75% cellular survival during 48 hour treatment at 4×MEC. Conversely, 22 (53.6%) compounds displayed ≥75% survival (75.1 to 100%) and were considered to either exhibit no- or low-level human cytotoxicity. It should be noted that 75% human cell survival was used as a culling criterion because it approximates the toxicity measures of the antibiotic, minocycline, when tested alone in these assays conditions (77.9% HepG2 survival at 2 µg ml$^{-1}$).

Example 5

Spectrum of Activity

Figure 3:
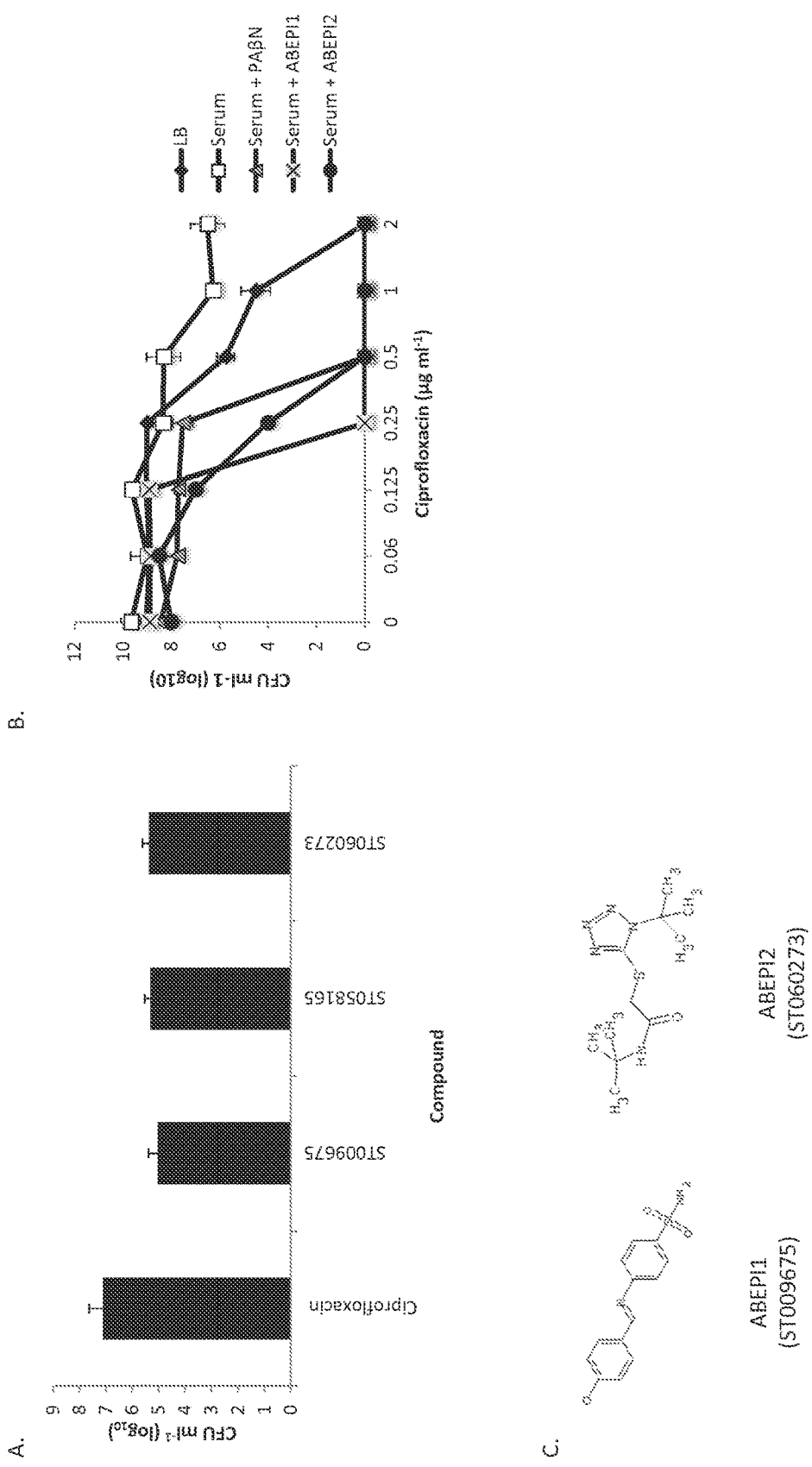
FIG. 3, Panel A is a graph demonstrating *A. baumannii* strain 98-37-09 growth in human serum supplemented with 0.125 μg ml$^{-1}$ ciprofloxacin, ST009675, ST058165, or ST060273.

As a means to further prioritize non-toxic compounds of interest based on their therapeutic promise, it was considered that broad spectrum antimicrobial efflux pump inhibitors may be more clinically valuable than narrow-spectrum agents that only potentiate the activity of a limited number of antibiotics or that display activity toward a single bacterial species. As described above, in addition to minocycline, *A. baumannii* growth in human serum also facilitates the efflux—and the organism's tolerance—of ciprofloxacin (FIG. 1A). Consequently, it was evaluated whether each compound potentiated the activity of ciprofloxacin toward serum grown cells. To do so, 1×10⁵ *A. baumannii* strain 98-37-09 were inoculated into individual wells of microtiter plates containing 100% human serum supplemented with 0.125 µg ml$^{-1}$ ciprofloxacin and 0, 1×, or 2× the compound's MEC, as defined by the lowest concentration needed to potentiated minocycline's antimicrobial effects (above). Plates were incubated for 48 hour at which point each compound's ability to potentiate ciprofloxacin was measured, as growth inhibition. Nineteen of the compounds evaluated did not affect the organism's tolerance to ciprofloxacin during these conditions, showing that they are narrow spectrum agents that limit minocycline, but not ciprofloxacin, efflux. Conversely, 3 compounds potentiated ciprofloxacin's antimicrobial activity, showing that they may represent broad spectrum antibiotic drug efflux pump inhibitors. Plating confirmed that, when administered in combination with ciprofloxacin, each compound reduced *A. baumannii* viability at least 1.5 log at 1× the compound's MEC, in comparison to cells treated with ciprofloxacin alone (FIG. 3A; Table 1).

It was also investigated whether the Gram-negative pathogens *Klebseilla pneumoniae* and *Pseudomonas aeruginosa* exhibit antibiotic tolerance to minocycline and/or ciprofloxacin during growth in human serum. While *K. pneumoniae* strain CKP4 did not, it was found that serum grown *P. aeruginosa* PA01 cells exhibit efflux mediated tolerance to ciprofloxacin, as described below. Thus, as an additional means to evaluate the spectrum of activity, and simultaneously identify highest priority compounds of interest that potentiate the activity of antibiotics across bacterial species, it was evaluated whether the aforementioned three putative broad-spectrum *A. baumannii* efflux pump inhibitors also inhibited *P. aeruginosa* serum-dependent ciprofloxacin tolerance. To do so, PA01 was inoculated into individuals wells of a microtiter plate containing 100% human serum supplemented with 1×MEC of test compound and increasing concentrations of ciprofloxacin (0 to 2 µg ml$^{-1}$) and cell viability was measured. Results revealed that two of the three putative broad-spectrum efflux pump inhibitors also potentiated the activity of ciprofloxacin toward serum grown *P. aeruginosa* (FIG. 3B), showing that these compounds, ABEPI1 and ABEPI1 (FIG. 3C), represent broad spectrum agents that may potentiate the antimicrobial properties of antibiotics toward at least two bacterial species of immediate healthcare concern, *A. baumannii* and *P. aeruginosa*.

To distinguish whether the antimicrobial potentiation of ABEPI1 and ABEPI2 correlates with the inhibition of *A. baumannii*'s efflux properties, conventional ethidium bromide efflux assays were performed in the presence and absence of each compound. The assay is predicated upon the fluorescent properties of ethidium bromide during intercalation into cellular nucleic acids, whereby efflux active cells display limited intracellular ethidium bromide accumulation and, consequently, low fluorescence. Conversely, efflux inhibition leads to increased cellular ethidium bromide levels and correspondingly high fluorescence relative to efflux proficient cells. Bacterial ethidium bromide efflux activity assays were used to measure the efflux inhibitory properties of compounds of interest. For assays, an overnight culture of *A. baumannii* strain 98-37-09 was diluted (1:100) into 100% human serum or fresh LB and grown to mid-exponential phase. Cell pellets were collected via centrifugation 900×g for 20 minutes, washed 3× with 20 mM sodium phosphate buffer and resuspended to an OD$_{600nm}$=0.2 in sodium phosphate buffer. Approximately 1×10⁶ CFU were loaded into individual wells of 96-well white-bottom plates, mixed with 10 µg ml$^{-1}$ ethidium bromide, and ethidium fluorescence (excitation 530$_{nm}$; emission 600$_{nm}$) was measured every 5 min for 90 min on a Spectramax5 fluorimeter (Molecular Devices, Sunnyvale, Calif.). To determine if the putative efflux pump inhibitors affected ethidium bromide efflux, cells were treated with the indicated amount of compound of interest or the efflux pump inhibitor, PaβN, two minutes after fluorescence monitoring began. Mock treated cells served as a negative control; plating confirmed that the test conditions used did not affect cell viability.

Figure 4:
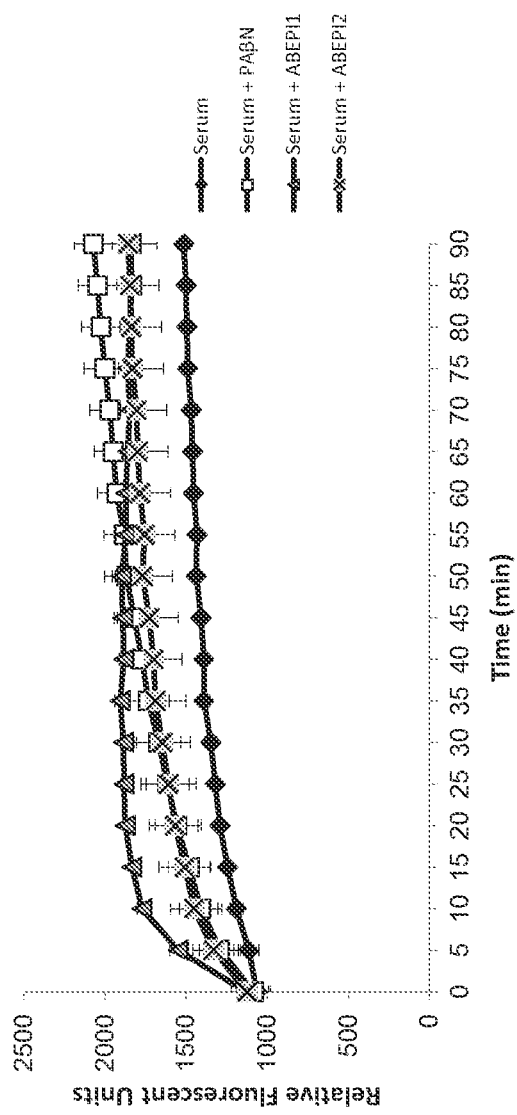
FIG. 4 shows the results of an ethidium bromide (EtBr) efflux assay demonstrating the inhibition of efflux in *A. baumannii* strain 98-37-09 by known EPI phenylalanine-arginine beta naphthylamide (PAβN, white squares), ABEPI1 (grey triangles), and ABEPI2 (grey x).

As shown in FIG. 4, mock treated cells displayed low-level ethidium bromide fluorescent signal that slowly increased during the course of the experiment, presumably reflecting the slow dye accumulation over time despite efflux pump activity. Conversely, efflux deficient PAβN treated cells exhibited significantly increased cellular ethidium bromide accumulation in comparison to mock treated cells, confirming that the assay conditions were appropriate to measure the efflux properties of *A. baumannii* cells. Likewise, both ABEPI1 and ABEPI2, displayed significantly increased signal in comparison to mock treated cells at all measured time points, indicating that they act as *A. baumannii* efflux pump inhibitors. More specifically, APEPI1 dramatically increased cellular fluorescence to levels exceeding that of PABN within the first 20 min of treatment, at which point the compound's potency appeared to level off. APEPI2 treatment measures were essentially identical to those of PAβN until approximately 35 min post-treatment at which point efflux inhibition appeared to drop below PAβN levels although the observed differences were not considered significantly different. Thus, ABEPI1 and ABEPI2 represent novel bacterial drug efflux inhibitors.

Example 6

Mammalian Calcium Channel Assays

Many laboratory bacterial efflux inhibitor tool compounds cannot be used in the clinical setting because they limit mammalian ion channel activity. Verapamil is one such agent, which effectively limits bacterial antibiotic efflux pumps but also elicits human neurotoxicity due to the inhibition of host $Ca^{2+}$ channels. Thus, we measured the effects of ABEPI1 and ABEPI2 on mammalian calcium channel functions using Fluo-4 Direct Calcium Channel Assay kits (Life Technologies, Carlsbad, Calif.), in which the dye Fluo-4 was used to measure changes in mammalian cytoplasmic $Ca^{2+}$ levels in response to the calcium channel stimulator, carbachol, in the absence and presence of test compound. Briefly, $5\times10^4$ human HEK 293T embryonic kidney cells were grown in individual wells of 96-well black-walled plates (COSTAR®, Corning Incorporated, Corning, N.Y.). Next, 2× Fluo-4 dye supplemented with Probenecid (5 mM) was added to each well and allowed to equilibrate for 1 hr at 37° C. To determine whether ABEPI1 or ABEPI2 affect $Ca^{2+}$ channel activity, Fluo-4 fluorescence measures (excitation $495_{nm}$; emission $516_{nm}$) were then taken every second for 15 sec. At that time point, cells were treated with either DMSO (mock), 50 µg $mL^{-1}$ of the $Ca^{2+}$ channel inhibitor verapamil (positive control) or 1×MEC ABEPI1 or ABEPI2 followed by the calcium channel stimulator carbamylocholine chloride (50 µg $ml^{-1}$; ThermoFisher Scientific, Waltham, Mass.) at 60 seconds and fluorescence was measured for an additional 120 seconds on a FlexStation 3 benchtop multimode microplate reader (Molecular Devices, Sunnyvale, Calif.).

Figure 5:
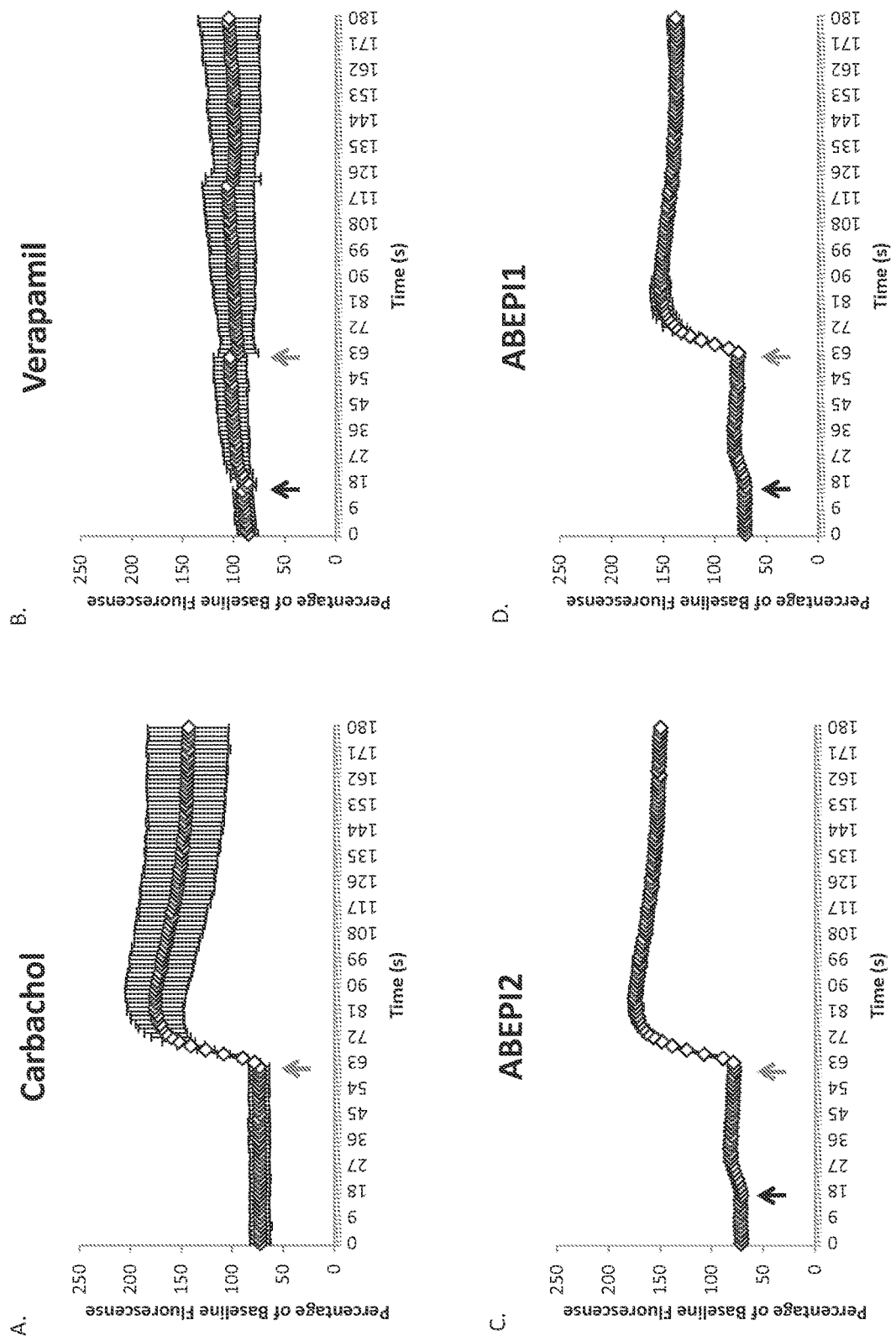
FIG. 5 contains the results from eukaryotic calcium channel inhibition assays. Human embryonic kidney cells (HEK 293T) cells were seeded into 96-well black walled plates and loaded with Fluo-4 calcium binding fluorophore.

FIG. 5A shows the profile of human embryonic kidney (HEK 293T) intracellular $Ca^{2+}$ levels prior to—and following—the addition of carbachol, which stimulates endoplasmic calcium-channel activity and, consequently, release of $Ca^{2+}$ into the cytoplasm. Carbachol treatment induced an approximately 2.3-fold increase in cytoplasmic $Ca^{2+}$ levels. Conversely, treatment of HEK 293T cells with the known calcium channel blocker, verapamil, virtually eliminated $Ca^{2+}$ channel activity and cytoplasmic accumulation, indicating that the system was appropriate for measuring mammalian cytoplasmic channel activity and inhibition (FIG. 5B). As shown in FIGS. 5C and 5D, HEK 293T treatment with 1×MEC of either ABEPI1 or ABEPI2 did not appear to significantly affect mammalian cell $Ca^{2+}$ channel stimulation in response to carbachol.

Taken together, ABEPI1 and ABEPI2 represent novel, structurally distinct molecules that potentiate the activity of antibiotics toward serum grown bacterial cells by inhibiting the organism's drug efflux properties, leading to cellular antibiotic accumulation and, consequently, antimicrobial effects. These compounds are effective as adjunctive efflux pump inhibitors to be used in combination with current antibiotics for improving the treatment of bacterial infections.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated. All publications, patents, and patent applications cited herein are hereby incorporated by reference in their entireties for all purposes.

What is claimed is:

1. A method for treating a microbial infection in a subject, comprising administering to the subject an effective amount of an efflux pump inhibitor of the following formula:

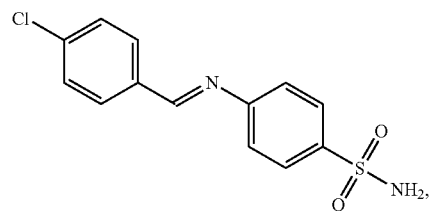 [SMILES: NS(=O)(=O)c1ccc(/N=C/c2ccc(Cl)cc2)cc1]

and
an antimicrobial agent.

2. The method of claim 1, further comprising selecting a subject infected with a microbe that is resistant to the antimicrobial agent.

3. The method of claim 2, wherein the resistance is mediated by an efflux pump.

4. The method of claim 1, wherein the microbial infection is a bacterial infection.

5. The method of claim 4, wherein the bacterial infection is a gram-negative bacterial infection.

6. The method of claim 4, wherein the bacterial infection is a gram-positive bacterial infection.

7. The method of claim 1, wherein the antimicrobial agent is selected from the group consisting of minocycline, ciprofloxacin, levofloxacin, nalidixic acid, amikacin, gentamycin, kanamycin, meropenem, ceftriaxone, erythromycin, colistin polymxin B, sulfamethoxazole, tigecycline, tobramycin, and trimethoprim.

8. The method of claim 1, wherein the efflux pump inhibitor and the antimicrobial agent are administered sequentially or simultaneously.

* * * * *